United States Patent
Yang et al.

(10) Patent No.: US 10,364,244 B2
(45) Date of Patent: Jul. 30, 2019

(54) CRYSTAL FORM OF PYRROLOQUINOLINE QUINONE SODIUM SALT AND PREPARATION METHOD AND USE THEREOF

(71) Applicant: Zhejiang Hisun Pharmaceutical Co., Ltd., Taizhou, Zhejiang (CN)

(72) Inventors: Zhiqing Yang, Taizhou (CN); Liang Zhang, Taizhou (CN); Xiangyang Zhang, Taizhou (CN); Zhenjuan Shi, Taizhou (CN); Min Zhao, Taizhou (CN); Hongying Luo, Taizhou (CN)

(73) Assignee: ZHEJIANG HISUN PHARMACEUTICAL CO., LTD., Zhejiang (CN)

( * ) Notice: Subject to any disclaimer, the term of this patent is extended or adjusted under 35 U.S.C. 154(b) by 0 days.

(21) Appl. No.: 15/762,895

(22) PCT Filed: Sep. 14, 2016

(86) PCT No.: PCT/CN2016/099013
§ 371 (c)(1),
(2) Date: Mar. 23, 2018

(87) PCT Pub. No.: WO2017/050171
PCT Pub. Date: Mar. 30, 2017

(65) Prior Publication Data
US 2018/0273526 A1    Sep. 27, 2018

(30) Foreign Application Priority Data

Sep. 25, 2015 (CN) .......................... 2015 1 0621701

(51) Int. Cl.
*A23L 33/10* (2016.01)
*A61Q 19/00* (2006.01)
(Continued)

(52) U.S. Cl.
CPC ............ *C07D 471/04* (2013.01); *A23L 33/10* (2016.08); *A61K 31/4745* (2013.01); *A61Q 19/00* (2013.01); *C07B 2200/13* (2013.01)

(58) Field of Classification Search
USPC .......................................................... 546/84
See application file for complete search history.

(56) References Cited

U.S. PATENT DOCUMENTS

2003/0216424 A1* 11/2003 Davis ................. A61K 31/4745
                                                          514/292
2012/0116087 A1*  5/2012 Edahiro ............... C07D 471/04
                                                          546/84
(Continued)

FOREIGN PATENT DOCUMENTS

CN        101553488 A     10/2009
CN        101885725 A     11/2010
(Continued)

OTHER PUBLICATIONS

Unverified Machine Translation of JP07113024, published Dec. 6, 1995. (Year: 1995).*

(Continued)

*Primary Examiner* — Daniel R Carcanague
(74) *Attorney, Agent, or Firm* — Armstrong Teasdale LLP

(57) ABSTRACT

Provided are crystal forms I, II, III and IV of a pyrroloquinoline quinone sodium salt and a preparation method thereof. Also provided are a pharmaceutical composition, a cosmetic composition, a functional food or a nutritional agent containing the above-mentioned crystal forms. The crystal forms have excellent properties in terms of solubility, crystal stability, hygroscopicity and the like.

6 Claims, 17 Drawing Sheets

(51) Int. Cl.
    *C07D 471/04*     (2006.01)
    *A61K 31/4745*    (2006.01)

(56) References Cited

U.S. PATENT DOCUMENTS

| | | | | |
|---|---|---|---|---|
| 2014/0128609 | A1* | 5/2014 | Ikemoto | C12P 7/66 546/84 |
| 2015/0291583 | A1* | 10/2015 | Zhu | C07D 471/04 514/292 |

FOREIGN PATENT DOCUMENTS

| | | | | |
|---|---|---|---|---|
| CN | 101228963 | B | 9/2011 | |
| CN | 102471336 | A | 5/2012 | |
| CN | 102942567 | A | 2/2013 | |
| CN | 103052391 | A | 4/2013 | |
| CN | 103119044 | A | 5/2013 | |
| CN | 103261197 | A | 8/2013 | |
| CN | 103619842 | A | 3/2014 | |
| JP | H07113024 | B2 | 12/1995 | |
| JP | 2751183 | B2 | 5/1998 | |
| JP | 2005530786 | A | 10/2005 | |
| JP | 2007269769 | A | 10/2007 | |
| JP | 2011219388 | * | 11/2011 | |
| JP | 2011246442 | A | 12/2011 | |
| JP | 2013112677 | * | 6/2013 | |
| WO | 2011007633 | A1 | 1/2011 | |
| WO | WO-2014071772 | A1* | 5/2014 | C07D 471/04 |
| WO | WO-2015159236 | A1* | 10/2015 | C07D 471/04 |

OTHER PUBLICATIONS

Unverified Machine Translation of CN101885725, published Nov. 17, 2010. (Year: 2010).*

Corey, E. J., et al., "Total synthesis of the quinonoid alcohol dehydrogenase coenzyme (1) of methylotrophic bacteria", J. Am. Chem. Soc., 1981, 103(18), pp. 5599-5600.

International Search Report issued in connection with International Application No. PCT/CN2016/099013 dated Dec. 15, 2016, 6 pages.

* cited by examiner

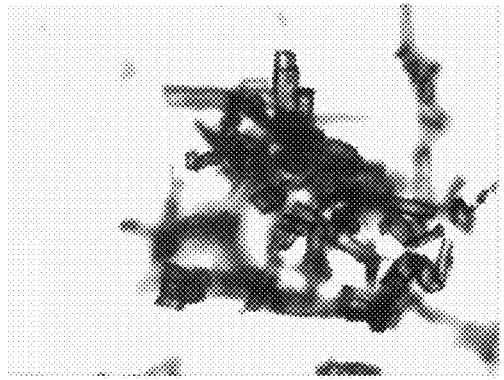

The crystal habit of the crystal form of pyrroloquinoline quinone disodium salt reported in CN201080031945

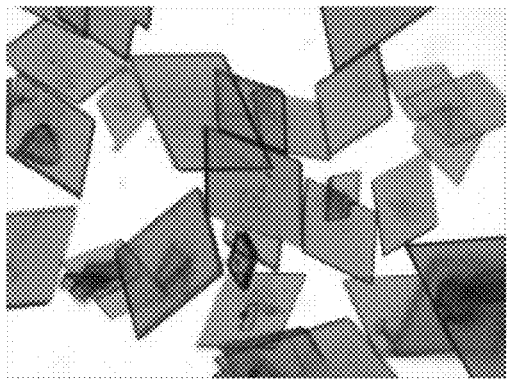

The crystal habit of the crystal form I of pyrroloquinoline quinone disodium salt

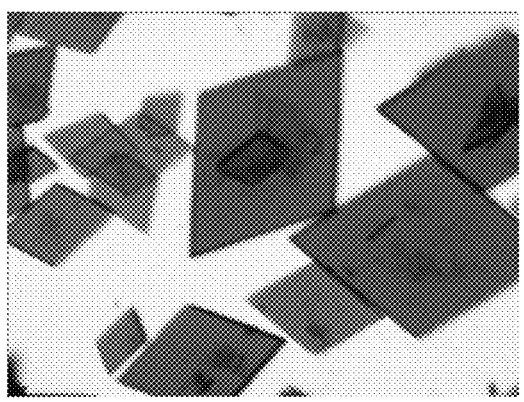

The crystal habit of the crystal form II of pyrroloquinoline quinone disodium salt

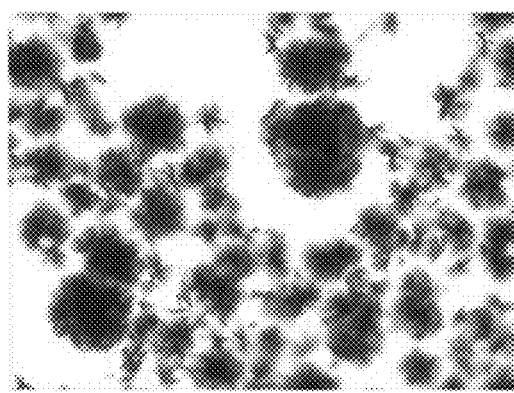

The crystal habit of the crystal form III of pyrroloquinoline quinone disodium salt

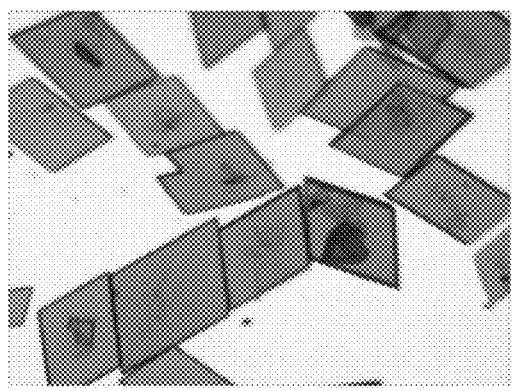

The crystal habit of the crystal form IV of pyrroloquinoline quinone monosodium salt

Figure 17

CRYSTAL FORM OF PYRROLOQUINOLINE QUINONE SODIUM SALT AND PREPARATION METHOD AND USE THEREOF

This application claims priority to International Application PCT/CN2016/099013, filed on Sep. 14, 2016, which claims priority to CN Patent Application No. 201510621701.1, filed on Sep. 25, 2015, the disclosures of which are hereby expressly incorporated by reference in their entireties.

TECHNICAL FIELD

The present invention relates to new crystal forms of pyrroloquinoline quinone sodium salt and preparation methods thereof, and the use of the new crystal forms in the fields of medicines, functional foods and cosmetics.

TECHNICAL BACKGROUND

Pyrroloquinoline quinone, the chemical name is 4,5-dihydro-4,5-dioxo-1H-pyrrolo[2,3-f]quinoline-2,7,9-tricarboxylic acid, also known as methaxatin; it has the following structural formula:

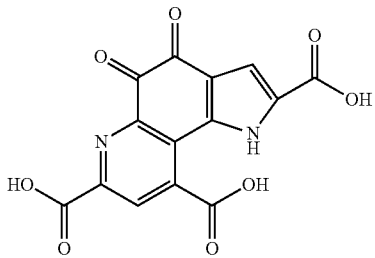 [SMILES: O=C(O)c1cc(C(=O)O)c2c(n1)C(=O)C(=O)c1cc(C(=O)O)[nH]c1-2]

Pyrroloquinoline quinone is a small molecule compound found in microorganisms, it is widely distributed in various tissues and organs of the human body and is called the fourteenth vitamin. It is widely used in the fields of medicines, functional foods and cosmetics. For example, pyrroloquinoline quinone can fully improve the body's immune function, in the field of medicines, pyrroloquinoline quinone can be used to prevent and cure liver damage, reduce damage of free radicals to the human body, conditioning a variety of nervous system diseases, promote the absorption of amino acids, promote the synthesis of growth factors, prevent and cure Alzheimer's disease, promote the synthesis of glutathione, and pyrroloquinoline quinone has a strong anti-cancer function. In addition, pyrroloquinoline quinone can be used as a health food with anti-aging effects in the field of foods; in the field of cosmetics, pyrroloquinoline quinone is an anti-allergic and skin-beautifying substance.

For polymorphic compounds, different crystal forms may have different physical and chemical properties; including melting point, chemical stability, apparent solubility, dissolution rate, optical and mechanical properties, etc. These physicochemical properties directly determine the effect of a specific crystal form in the fields of medicines, functional foods, cosmetics and the like. For example, the crystal form of the pyrroloquinoline quinone sodium salt obtained by the prior art method is unstable and has a high hygroscopicity and a large extent of variation of humidity within the temperature range of storage at normal temperature, and the solid state is not ideal and is not suitable for processing (filtering, drying, tabletting), thus adversely affecting the application and storage of the pyrroloquinoline quinone sodium salt. In the prior art, some modifications are made to the crystal form of pyrroloquinoline quinone sodium salt, for example, in the patent CN201080031945, the invention overcomes the defects of low crystallinity and high content of residual solvent reported in some literatures, but the prepared crystal form also has hygroscopicity, the crystal form A in CN201210452297.6 has improved hygroscopicity, the hygroscopicity is less than 3%, preferably less than 0.6% at 65%-85% RH, but such hygroscopicity still cannot satisfy the need of the preparation process that has high requirement on hygroscopicity of crystal forms.

Therefore, although some crystal forms of pyrroloquinoline quinone have been disclosed in the prior art (in addition to the two literatures that are mentioned above, the prior art includes but is not limited to the following literatures, JP 2005-530786 A, JP 2011-246442 A, JP 2007-269769 A, WO2011/007633, JPH07113024(B2), CN201280028888.9), there is still a need to develop a new crystal form that has better properties than the known crystal forms, and has broad application prospects. Compared with the prior art, the crystal form provided by the present invention has lower hygroscopicity and the hygroscopixity is less than 0.3%, preferably no hygroscopixity at 75% RH.

The present invention aims at providing a crystal form with high crystallinity, high product purity and low content of residual solvent, which is easy to be filtered, dried and stored, as well as providing an environment-friendly and pollution-free process.

SUMMARY OF THE INVENTION

In a first aspect, the present invention aims to provide new crystal forms of pyrroloquinoline quinone sodium salt that have excellent chemical and physical stabilities and have excellent properties in terms of solubility, crystal form stability, hygroscopicity and processing (filtering, drying, tabletting) adaptability. In a second aspect, the present invention aims to provide the preparation methods of the new crystal forms of pyrroloquinoline quinone sodium salt, and in the third aspect, the present invention aims to provide pharmaceutical compositions, cosmetic compositions, functional foods or nutritional agents that comprise these new crystal forms and use of the crystal forms in the fields of medicines, functional foods and cosmetics.

In the first aspect, the present invention provides a new crystal form I of pyrroloquinoline quinone disodium salt, the crystal form I has characteristic peaks at the following 2θ diffraction angles in the X-ray powder diffraction (XRPD) pattern: 8.0±0.2°, 10.9±0.2°, 11.2±0.2°, 15.1±0.2°, 15.8±0.2°, 22.4±0.2°, 25.5±0.2°, 27.7±0.2°.

Further, in another embodiment of the present invention, the crystal form I of pyrroloquinoline quinone disodium salt of the present invention also has characteristic peaks at the following 2θ diffraction angles: 16.9±0.2°, 18.2±0.2°, 20.6±0.2°, 21.5±0.2°, 23.7±0.2°, 26.0±0.2°, 27.3±0.2°, 28.1±0.2°, 28.5±0.2°, 29.8±0.2°.

In one embodiment of the present invention, the X-ray powder diffraction pattern of the crystal form I of pyrroloquinoline quinone disodium salt of the present invention has data of 2θ angles, d-values, relative intensities of the characteristic peaks as shown in Table 1 below:

TABLE 1

| Peak No. | 2θ(°) | d(Å) | Relative intensity(%) |
|---|---|---|---|
| 1 | 8.0 | 11.1 | 100 |
| 2 | 10.9 | 8.1 | 22.1 |
| 3 | 11.2 | 7.9 | 9.4 |
| 4 | 15.1 | 5.9 | 4.0 |
| 5 | 15.8 | 5.6 | 14.1 |
| 6 | 16.9 | 5.2 | 1.7 |
| 7 | 18.2 | 4.9 | 8.1 |
| 8 | 20.6 | 4.3 | 2.2 |
| 9 | 21.5 | 4.1 | 5.1 |
| 10 | 22.4 | 4.0 | 16.8 |
| 11 | 23.7 | 3.7 | 7.2 |
| 12 | 25.5 | 3.5 | 14.6 |
| 13 | 26.0 | 3.4 | 7.5 |
| 14 | 27.3 | 3.3 | 5.7 |
| 15 | 27.7 | 3.2 | 47.9 |
| 16 | 28.1 | 3.2 | 10.2 |
| 17 | 28.5 | 3.1 | 11.9 |
| 18 | 29.8 | 3.0 | 4.2 |

TABLE 2

| Peak No. | 2θ(°) | d(Å) | Relative intensity(%) |
|---|---|---|---|
| 1 | 7.8 | 11.3 | 100 |
| 2 | 8.9 | 9.9 | 17.5 |
| 3 | 10.1 | 8.8 | 5.8 |
| 4 | 10.8 | 8.2 | 52.9 |
| 5 | 11.1 | 8.0 | 32.6 |
| 6 | 15.0 | 5.9 | 7.6 |
| 7 | 15.6 | 5.7 | 13.1 |
| 8 | 18.0 | 4.9 | 17.6 |
| 9 | 20.7 | 4.3 | 7.2 |
| 10 | 21.6 | 4.1 | 10.3 |
| 11 | 22.2 | 4.0 | 26.3 |
| 12 | 23.5 | 3.8 | 16.4 |
| 13 | 24.4 | 3.6 | 6.1 |
| 14 | 25.3 | 3.5 | 14.2 |
| 15 | 26.0 | 3.4 | 11.8 |
| 16 | 26.6 | 3.3 | 9.8 |
| 17 | 27.5 | 3.2 | 88.8 |
| 18 | 28.2 | 3.2 | 33.4 |

Unrestrictedly, the crystal form I of pyrroloquinoline quinone disodium salt of the present invention has an X-ray powder diffraction pattern as shown in FIG. 1.

The crystal form I of pyrroloquinoline quinone disodium salt of the present invention can be characterized by an infrared absorption spectrum measured by using a KBr pellet, the infrared absorption spectrum has characteristic peaks at about 3502.68 cm$^{-1}$, 3075.00 cm$^{-1}$, 1745.31 cm$^{-1}$, 1720.24 cm$^{-1}$, 1662.49 cm$^{-1}$, 1607.36 cm$^{-1}$, 1542.24 cm$^{-1}$, 1505.77 cm$^{-1}$, 1372.28 cm$^{-1}$, 1300.29 cm$^{-1}$, 1280.01 cm$^{-1}$, 1260.47 cm$^{-1}$, 1220.80 cm$^{-1}$, 1202.86 cm$^{-1}$, 1176.23 cm$^{-1}$, 971.91 cm$^{-1}$, 940.36 cm$^{-1}$, 886.67 cm$^{-1}$, 812.19 cm$^{-1}$, 792.93 cm$^{-1}$, 770.80 cm$^{-1}$, 747.86 cm$^{-1}$, 702.98 cm$^{-1}$, 610.52 cm$^{-1}$, 538.17 cm$^{-1}$, 430.94 cm$^{-1}$.

Further, in another embodiment of the present invention, the infrared absorption spectrum of the crystal form I of pyrroloquinoline quinone disodium salt of the present invention also has characteristic peaks at about 1431.23 cm$^{-1}$, 1398.99 cm$^{-1}$, 1144.92 cm$^{-1}$, 1082.92 cm$^{-1}$.

Unrestrictedly, the crystal form I of pyrroloquinoline quinone disodium salt of the present invention has an infrared absorption spectrum as shown in FIG. 2.

Unrestrictedly, the crystal form I of pyrroloquinoline quinone disodium salt of the present invention has a differential scanning calorimetry (DSC) thermogram as shown in FIG. 3.

Unrestrictedly, the crystal form I of pyrroloquinoline quinone disodium salt of the present invention has a thermogravimetric analysis (TGA) thermogram as shown in FIG. 4.

In the first aspect, the present invention provides a new crystal form II of pyrroloquinoline quinone disodium salt, the crystal form II has characteristic peaks at the following 2θ diffraction angles in the X-ray powder diffraction (XRPD) pattern: 7.8±0.2°, 10.8±0.2°, 11.1±0.2°, 22.2±0.2°, 27.5±0.2°.

Further, in another embodiment of the present invention, the crystal form II of pyrroloquinoline quinone disodium salt of the present invention also has characteristic peaks at the following 2θ diffraction angles: 8.9±0.2°, 15.6±0.2°, 18.0±0.2°, 23.5±0.2°, 28.2±0.2°.

In one embodiment of the present invention, the X-ray powder diffraction pattern of the crystal form II of pyrroloquinoline quinone disodium salt of the present invention has data of 2θ angles, d-values, relative intensities as shown in Table 2 below:

Unrestrictedly, the crystal form II of pyrroloquinoline quinone disodium salt of the present invention has an X-ray powder diffraction pattern as shown in FIG. 5.

The crystal form II of pyrroloquinoline quinone disodium salt of the present invention can be characterized by an infrared absorption spectrum measured by using a KBr pellet, the infrared absorption spectrum has characteristic peaks at about 1719.04 cm$^{-1}$, 1667.65 cm$^{-1}$, 1610.08 cm$^{-1}$, 1541.60 cm$^{-1}$, 1503.07 cm$^{-1}$, 1279.55 cm$^{-1}$, 1222.19 cm$^{-1}$, 1142.30 cm$^{-1}$, 1079.27 cm$^{-1}$, 963.60 cm$^{-1}$, 938.81 cm$^{-1}$, 792.11 cm$^{-1}$, 771.05 cm$^{-1}$, 702.30 cm$^{-1}$, 609.59 cm$^{-1}$, 535.29 cm$^{-1}$, 429.20 cm$^{-1}$, 411.27 cm$^{-1}$.

Further, in another embodiment of the present invention, the crystal form II of the pyrroloquinoline quinone disodium salt of the present invention also has characteristic peaks at about 3499.74 cm$^{-1}$, 3122.28 cm$^{-1}$, 3074.36 cm$^{-1}$, 2560.88 cm$^{-1}$, 2360.30 cm$^{-1}$, 1744.02 cm$^{-1}$, 1397.72 cm$^{-1}$, 888.38 cm$^{-1}$.

Unrestrictedly, the crystal form II of pyrroloquinoline quinone disodium salt of the present invention has an infrared absorption spectrum as shown in FIG. 6.

Unrestrictedly, the crystal form II of pyrroloquinoline quinone disodium salt of the present invention has a DSC thermogram as shown in FIG. 7.

Unrestrictedly, the crystal form II of pyrroloquinoline quinone disodium salt of the present invention has a TGA thermogram as shown in FIG. 8.

In the first aspect, the present invention provides a new crystal form III of pyrroloquinoline quinone disodium salt, the crystal form III has characteristic peaks at the following 2θ diffraction angles in the X-ray powder diffraction (XRPD) pattern: 7.4±0.2°, 8.6±0.2°, 14.0±0.2°, 14.6±0.2°, 19.9±0.2°, 21.4±0.2°, 26.0±0.2°, 27.3±0.2°, 28.5±0.2°.

The X-ray powder diffraction pattern of the crystal form III of pyrroloquinoline quinone disodium salt of the present invention has data of 2θ angles, d-values, relative intensities as shown in Table 3 below:

TABLE 3

| Peak No. | 2θ(°) | d(Å) | Relative intensity (%) |
|---|---|---|---|
| 1 | 7.4 | 12.0 | 67.4 |
| 2 | 8.6 | 10.3 | 100 |
| 3 | 14.0 | 6.3 | 20.9 |
| 4 | 14.6 | 6.1 | 14.1 |
| 5 | 15.8 | 5.6 | 3.9 |
| 6 | 17.1 | 5.2 | 3.2 |

TABLE 3-continued

| Peak No. | 2θ(°) | d(Å) | Relative intensity (%) |
|---|---|---|---|
| 7 | 18.9 | 4.7 | 2.1 |
| 8 | 19.9 | 4.4 | 27.5 |
| 9 | 21.4 | 4.2 | 7.4 |
| 10 | 22.7 | 3.9 | 8.7 |
| 11 | 24.2 | 3.7 | 3.6 |
| 12 | 24.6 | 3.6 | 2.9 |
| 13 | 26.0 | 3.4 | 8.2 |
| 14 | 27.3 | 3.3 | 50.7 |
| 15 | 28.5 | 3.1 | 14.7 |

Unrestrictedly, the crystal form III of pyrroloquinoline quinone disodium salt of the present invention has an X-ray powder diffraction pattern as shown in FIG. 9.

The crystal form III of pyrroloquinoline quinone disodium salt of the present invention can be characterized by an infrared absorption spectrum measured by using a KBr pellet, the infrared absorption spectrum has characteristic peaks at about 3446.06 cm$^{-1}$, 1721.16 cm$^{-1}$, 1680.19 cm$^{-1}$, 1613.68 cm$^{-1}$, 1541.14 cm$^{-1}$, 1496.91 cm$^{-1}$, 1349.99 cm$^{-1}$, 1243.04 cm$^{-1}$, 940.32 cm$^{-1}$, 722.10 cm$^{-1}$, 562.47 cm$^{-1}$, 424.89 cm$^{-1}$.

Further, in another embodiment of the present invention, the crystal form III of the pyrroloquinoline quinone disodium salt of the present invention also has characteristic peaks at about 1077.39 cm$^{-1}$, 801.05 cm$^{-1}$, 749.60 cm$^{-1}$.

Unrestrictedly, the crystal form III of pyrroloquinoline quinone disodium salt of the present invention has an infrared absorption spectrum as shown in FIG. 10.

Unrestrictedly, the crystal form III of pyrroloquinoline quinone disodium salt of the present invention has a DSC thermogram as shown in FIG. 11.

Unrestrictedly, the crystal form III of pyrroloquinoline quinone disodium salt of the present invention has a TGA thermogram as shown in FIG. 12.

In the first aspect, the present invention provides a new crystal form IV of pyrroloquinoline quinone monosodium salt, the crystal form IV has characteristic peaks at the following 2θ diffraction angles in the X-ray powder diffraction (XRPD) pattern: 7.8±0.2°, 10.8±0.2°, 15.1±0.2°, 15.7±0.2°, 16.9±0.2°, 18.2±0.2°, 20.6±0.2°, 27.7±0.2°, 28.4±0.2°.

Further, in another embodiment of the present invention, the crystal form IV of pyrroloquinoline quinone monosodium salt of the present invention also has characteristic peaks at the following 2θ diffraction angles: 18.0±0.2°, 22.3±0.2°, 23.6±0.2°, 25.4±0.2°, 25.8±0.2°.

In one embodiment of the present invention, the X-ray powder diffraction pattern of the crystal form IV of pyrroloquinoline quinone monosodium salt of the present invention has data of 2θ angles, d-values, relative intensities as shown in Table 4 below:

TABLE 4

| Peak No. | 2θ(°) | d(Å) | Relative intensity(%) |
|---|---|---|---|
| 1 | 7.8 | 11.3 | 42.7 |
| 2 | 10.8 | 8.2 | 40.2 |
| 3 | 12.6 | 7.0 | 2.3 |
| 4 | 13.2 | 6.7 | 3.2 |
| 5 | 15.1 | 5.9 | 8.0 |
| 6 | 15.7 | 5.6 | 9.9 |
| 7 | 16.9 | 5.3 | 5.5 |
| 8 | 18.0 | 4.9 | 10.8 |
| 9 | 18.2 | 4.9 | 18.1 |
| 10 | 20.6 | 4.3 | 6.8 |
| 11 | 21.6 | 4.1 | 11.0 |
| 12 | 22.3 | 4.0 | 15.4 |
| 13 | 23.6 | 3.8 | 10.2 |
| 14 | 24.4 | 3.6 | 6.0 |
| 15 | 25.4 | 3.5 | 22.7 |
| 16 | 25.8 | 3.5 | 13.0 |
| 17 | 27.7 | 3.2 | 100 |
| 18 | 28.4 | 3.1 | 34.0 |

Unrestrictedly, the crystal form IV of pyrroloquinoline quinone monosodium salt of the present invention has an X-ray powder diffraction pattern as shown in FIG. 13.

The crystal form IV of pyrroloquinoline quinone monosodium salt of the present invention can be characterized by an infrared absorption spectrum measured by using a KBr pellet, the infrared absorption spectrum has characteristic peaks at about 3503.09 cm$^{-1}$, 3074.74 cm$^{-1}$, 1744.71 cm$^{-1}$, 1720.37 cm$^{-1}$, 1664.30 cm$^{-1}$, 1606.88 cm$^{-1}$, 1544.10 cm$^{-1}$, 1505.39 cm$^{-1}$, 1398.65 cm$^{-1}$, 1301.22 cm$^{-1}$, 1280.13 cm$^{-1}$, 1259.72 cm$^{-1}$, 1202.57 cm$^{-1}$, 1176.96 cm$^{-1}$, 1144.49 cm$^{-1}$, 1082.30 cm$^{-1}$, 970.03 cm$^{-1}$, 939.56 cm$^{-1}$, 793.39 cm$^{-1}$, 770.25 cm$^{-1}$, 748.91 cm$^{-1}$, 717.95 cm$^{-1}$, 608.86 cm$^{-1}$, 536.98 cm$^{-1}$, 430.96 cm$^{-1}$.

Unrestrictedly, the crystal form IV of pyrroloquinoline quinone monosodium salt of the present invention has an infrared absorption spectrum as shown in FIG. 14.

Unrestrictedly, the crystal form IV of pyrroloquinoline quinone monosodium salt of the present invention has a DSC thermogram as shown in FIG. 15.

Unrestrictedly, the crystal form IV of pyrroloquinoline quinone monosodium salt of the present invention has a TGA thermogram as shown in FIG. 16.

In the second aspect, the present invention provides a preparation method of said crystal form I of pyrroloquinoline quinone disodium salt, said method comprises:

(1) using pyrroloquinoline quinone as solute, pure water or ethanol/water as solvent;
(2) adjusting the pH to 1-2;
(3) crystallizing with stirring;
(4) continue to adjust the pH to 3-4;
(5) filtering to give the crystal form I of pyrroloquinoline quinone disodium salt.

The weight-to-volume ratio (g/ml) of pyrroloquinoline quinone to the mixed solvent is preferably from 1:10 to 1:400, more preferably from 1:50 to 1:200 when water or ethanol/water is used as solvent, wherein, the state of the liquid for crystallization described in (1) can be clear or pyrroloquinoline quinone can be suspended in the liquid; the temperature of the liquid is controlled at 15° C.-60° C., preferably 25° C.-50° C.

In the second aspect, the present invention also provides a preparation method of said crystal form II of pyrroloquinoline quinone disodium salt, said method comprises: drying the crystal form I of pyrroloquinoline quinone disodium salt at 30° C.-60° C. under vacuum condition to obtain crystal form II.

In the second aspect, the present invention also provides a preparation method of said crystal form III of pyrroloquinoline quinone disodium salt, said method comprises:

(1) adding pyrroloquinoline quinone to a mixed solvent of ethanol/water;
(2) stirring, dissolving with the temperature increased;
(3) filtering, reducing the temperature, adjusting the pH to 3-4;

(4) crystallizing;
(5) filtering to give the crystal form III of pyrroloquinoline quinone disodium salt.

The weight-to-volume ratio (g/ml) of pyrroloquinoline quinone to the mixed solvent is preferably from 1:200 to 1:400 when ethanol/water is used as solvent, wherein the volume ratio of ethanol to water is 1:1-3:1, the temperature of crystallization is controlled at 0° C.-20° C., preferably 5° C.-15° C.

In the second aspect, the present invention also provides a preparation method of said crystal form IV of pyrroloquinoline quinone monosodium salt, said method comprises:

(1) using pyrroloquinoline quinone as solute, pure water or ethanol/water as solvent;
(2) adjusting the pH to 1-2;
(3) crystallizing with stirring;
(4) filtering to give the crystal form IV of pyrroloquinoline quinone monosodium salt.

Wherein, the state of the liquid for crystallization described in (1) can be clear or pyrroloquinoline quinone can be suspended in the liquid; the temperature of the liquid is controlled at 15° C.-60° C., preferably 25° C.-50° C.

In the above method, the unit of the weight-volume ratio of the pyrroloquinoline quinone to the corresponding solvent can be g/ml, Kg/L and the like, depending on the specific operation scale.

In the third aspect, the present invention provides pharmaceutical compositions, cosmetic compositions, functional foods or nutritional agents comprising the new crystal forms of the present invention and use of the new crystal forms in the fields of medicines, functional foods and cosmetics.

The raw material, pyrroloquinoline quinone used in the methods of the present invention can be commercially available or can be prepared according to known methods. There are no special limitations of the solvents used in the present invention, common solvents that are commercially available can be used.

Unless otherwise specified, the "stirring" in the method of the present invention can be carried out by conventional methods in the art, for example, stirring method includes magnetic stirring and mechanical stirring.

The X-ray powder diffractometer (XRPD) and the test conditions involved in the present invention are: X-ray powder diffractometer model Rigaku D/max-2200Cu target; operation method: scanning speed 4°/min, scanning step width 0.01°.

The infrared spectrophotometer and the test conditions involved in the present invention are: infrared spectrophotometer model: BRWKER JECTOR 22; operation method: using KBr pellet method, scanning range 400-4000 cm$^{-1}$.

The test conditions for differential scanning calorimetry (DSC) involved in the present invention are: differential scanning calorimeter model: NETZSCH DSC200F3 Jaia; operation method: heating rate 10° C./min, temperature range: 30-250° C.

The test conditions for thermogravimetric analysis (TGA) involved in the present invention are: thermogravimetric analyzer model: PerkinElmer TGA400; operation method: heating rate 10° C./min, temperature range: 30-300° C.

The test conditions for microscope are: microscope model: OLYMPUS CX31; operation method: eyepiece 10×, objective lens 10×.

The test conditions for liquid chromatography involved in the present invention are: chromatographic column: Ultimate LP-C18 (Welch Materials), 4.6×250 mm, 5 μm; phase A: 5 mM monopotassium phosphate, the pH is adjusted to 2.2 with phosphoric acid; phase B: pure acetonitrile; detection wavelength: 251 nm; flow rate: 1.0 ml/min; injection volume: 10 μl; column temperature: 30° C., the conditions for liquid chromatograph yare shown in Table 5:

TABLE 5

| t (min) | A(%) | B(%) |
|---|---|---|
| 0.0 min | 93 | 7% |
| 2.0 min | 93 | 7% |
| 15.0 min | 85 | 15% |
| 30.0 min | 75 | 25% |
| 31.0 min | 70 | 30% |
| 40.0 min | 70 | 30% |
| 40.1 min | 93 | 7% |
| 59.0 min | 93 | 7% |

It should be emphasized that the meaning or the intended protection scope of the numerical values or numerical endpoints involved in the technical solutions of the present invention are not limited to the numbers themselves, and those skilled in the art should understand that they include those allowable ranges of errors that have been widely accepted in the art, such as experimental errors, measurement errors, statistical errors and random errors etc., and the ranges of these errors are all included in the scope of the present invention.

In addition, the present invention also provides pictures of the crystal habits of pyrroloquinoline quinone sodium salt under the microscope. As shown in FIG. 17, wherein the crystal habit of the crystal form I of pyrroloquinoline quinone disodium salt is rhombohedral, the crystal form II is prepared by drying crystal form I and the crystal habit does not change, the crystal habit of crystal form IV is consistent with that of crystal form I. From the pictures, it can be seen that the crystal habit of crystal form I is regular, and the crystal form I has good solid fluidity, is easy to be filtered and dried. In addition, the crystals obtained by crystallization have high purity, poor hygroscopicity, and good stability and are easy to be stored.

BRIEF DESCRIPTION OF THE DRAWINGS

FIG. 17 shows pictures of crystal habits of pyrroloquinoline quinone sodium salts.

EMBODIMENTS

The following examples further illustrate the present invention, however, they do not constitute a limitation on the scope of the present invention.

The crude pyrroloquinoline quinone used in the present invention is pyrroloquinoline quinone trisodium salt, which can be prepared by using conventional methods in the art: for example, the crude pyrroloquinoline quinone can be prepared by the methods in the patent document CN101228963B or the document J. Am. Chem. Soc., 1981, 103, 5599-5600.

Preparation of pyrroloquinoline quinone trisodium salt solution in Example 1 and Example 14: a pyrroloquinoline quinone fermentation broth was prepared by the method of the Japanese Patent No. 2751183, the pH of the fermentation broth was adjusted to 9-10, followed by column treatment (the sample was added to a silica gel column, silica gel 200-300 mesh, alcohol-soluble impurities were eluted with ethanol, and then the material was eluted with water, the purified sample solution was collected), the resulting solution was pyrroloquinoline quinone trisodium salt solution.

EXAMPLES

Example 1

The pyrroloquinoline quinone trisodium salt solution 100 g (HPLC purity >98%, concentration 0.7%) was heated up to 40° C., stirring was continued for 30 min, the pH was adjusted to 1.0-2.0; filtered to give a clear filtrate, the temperature of the filtrate was decreased to 25° C. with a rate of 10° C./h and the filtrate was crystallized under stirring at 25° C. for 12 h, the pH was adjusted to 3.0-4.0; stirred, filtered, dried at 25° C. under vacuum to give 0.45 g crystals, purity was 99.1% by HPLC, X-ray powder diffraction pattern showed a new crystal form.

Figure 1:
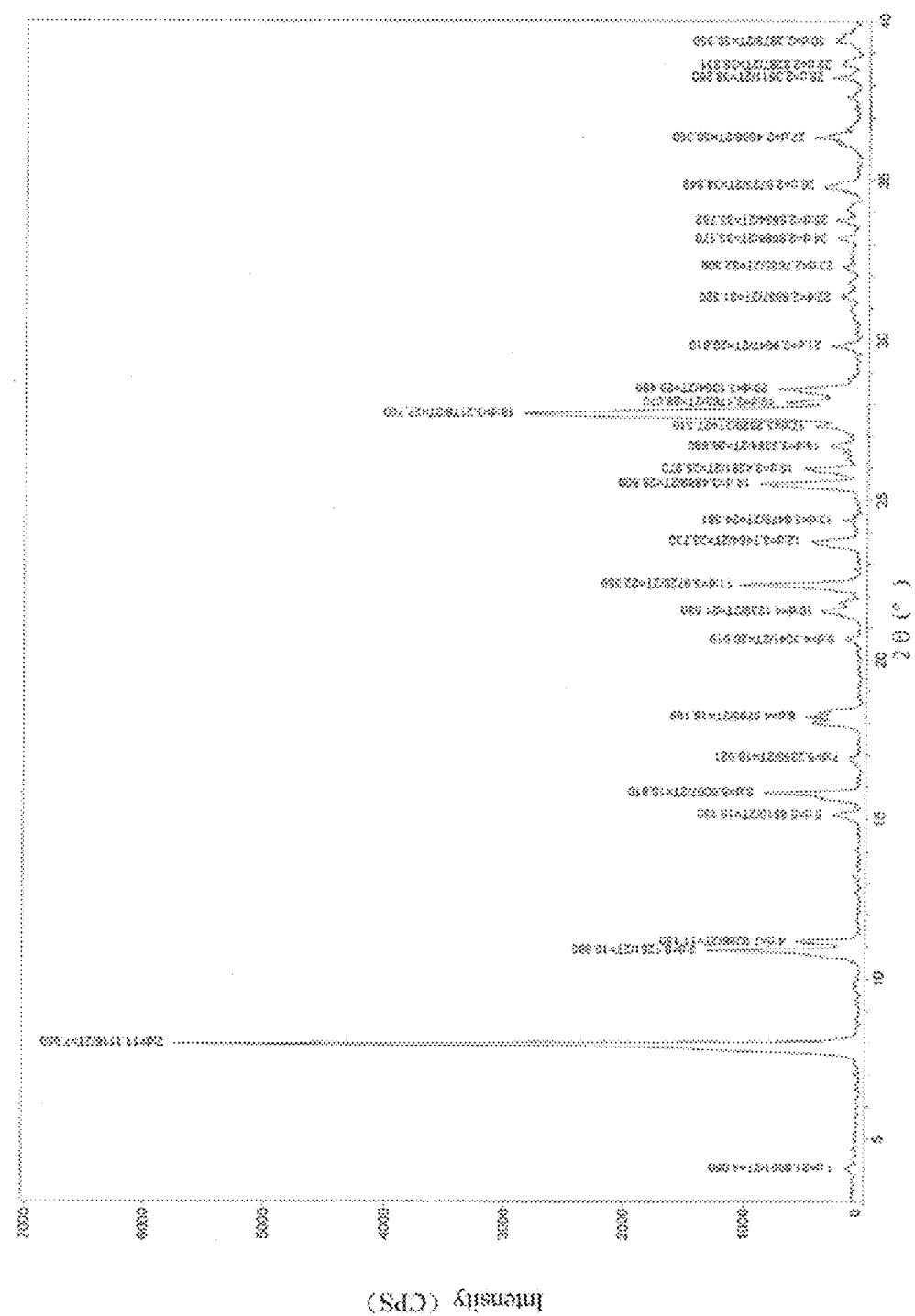
FIG. 1 is an X-ray powder diffraction pattern of crystal form I of pyrroloquinoline quinone disodium salt obtained in Example 1.
Figure 2:
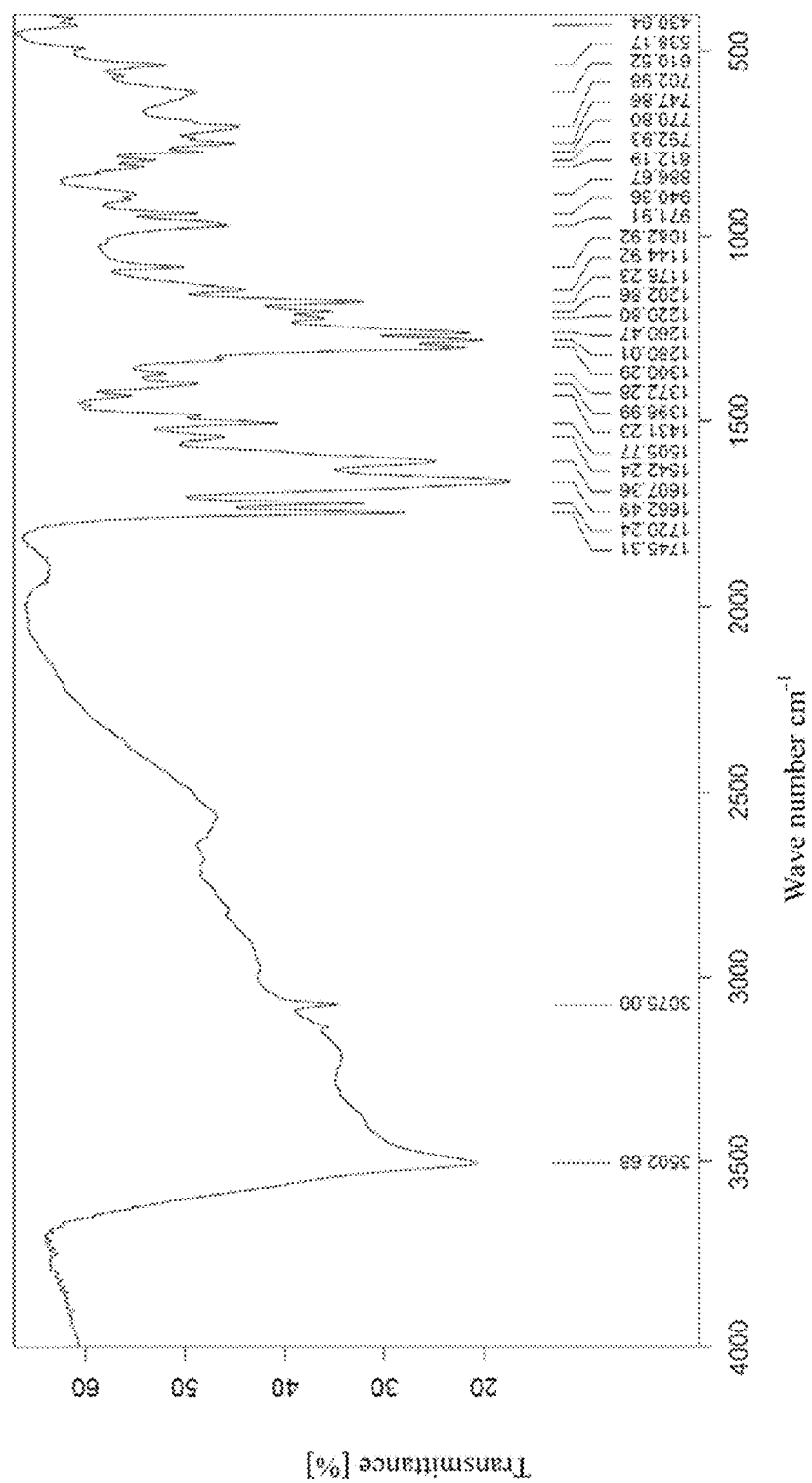
FIG. 2 is an infrared absorption spectrum of crystal form I of pyrroloquinoline quinone disodium salt obtained in Example 1.
Figure 3:
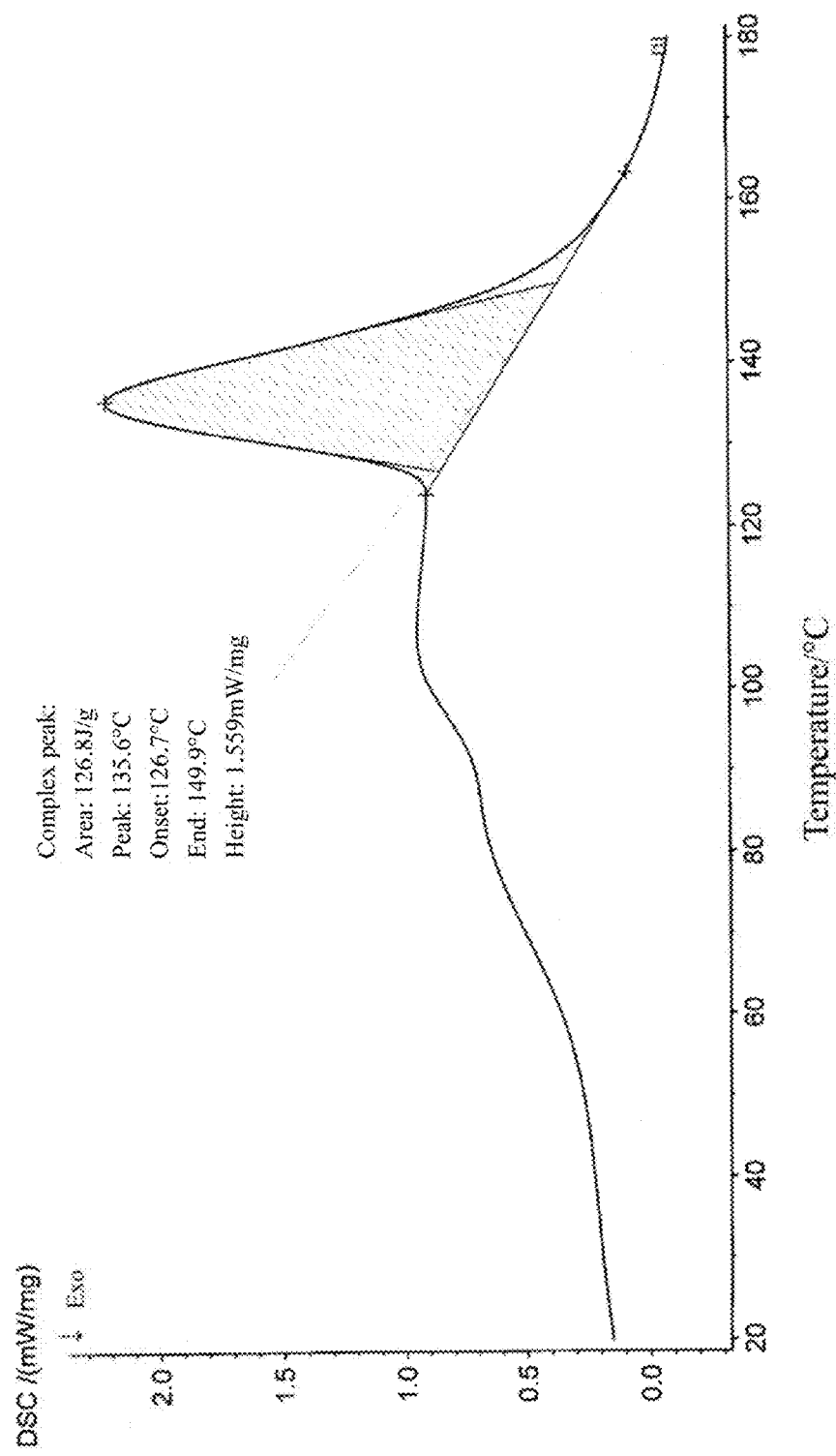
FIG. 3 is a DSC thermogram of crystal form I of pyrroloquinoline quinone disodium salt obtained in Example 1.
Figure 4:
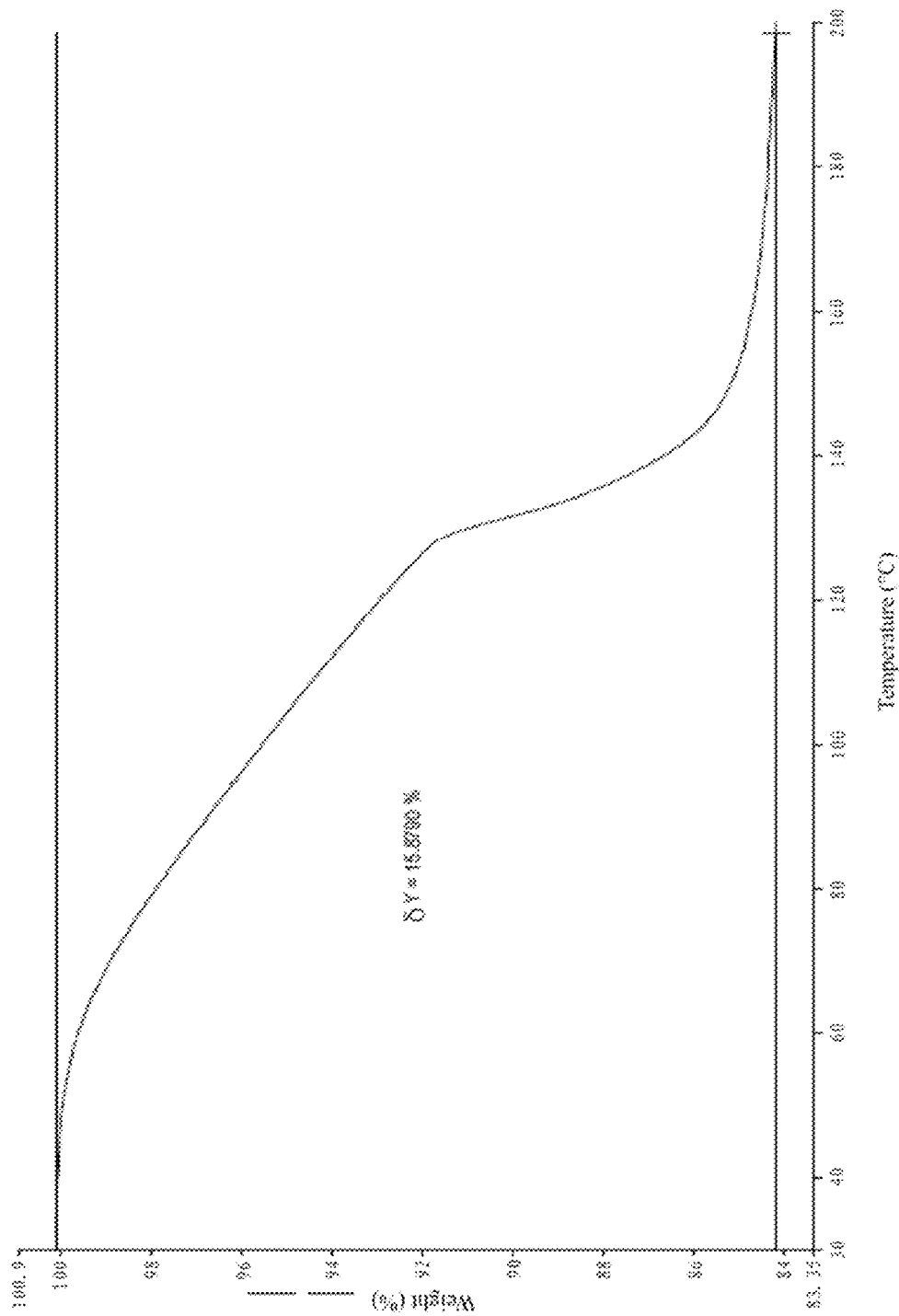
FIG. 4 is a TGA thermogram of crystal form I of pyrroloquinoline quinone disodium salt obtained in Example 1.

The X-ray powder diffraction pattern, the infrared absorption spectrum, DSC thermogram and TGA thermogram of the crystal form are detailed in FIGS. 1-4, the crystal form is named as crystal form I of pyrroloquinoline quinone disodium salt in the present invention.

Example 2

The crude pyrroloquinoline quinone 1 g (HPLC purity >98%) was dissolved in 100 mL of water, the temperature was increased to 60° C., stirring was continued for 30 min, dissolved; filtered, the pH was adjusted to 1.0-2.0; filtered to give a clear filtrate, the temperature of the filtrate was decreased to 25° C. with a rate of 10° C./h and the filtrate was crystallized under stirring at 25° C. for 48 h, the pH was adjusted to 3.0-4.0; stirred, filtered, dried at 25° C. under vacuum to give 0.62 g crystals, purity was 98.8% by HPLC, X-ray powder diffraction pattern showed crystal form I.

Example 3

The crude pyrroloquinoline quinone 1 g (HPLC purity >98%) was dissolved in 100 mL of water, the temperature was increased to 40° C., stirring was continued for 30 min, dissolved; filtered, the temperature was decreased to 15° C., the pH was adjusted to 1.0-2.0; the temperature was increased to 45° C. and the filtrate was crystallized under stirring at 45° C. for 12 h, the pH was adjusted to 3.0-4.0; stirred, filtered, dried at 25° C. under vacuum to give 0.61 g crystals, purity was 99.2% by HPLC, X-ray powder diffraction pattern showed crystal form I.

Example 4

The crude pyrroloquinoline quinone 1 g (HPLC purity >98%) was dissolved in 100 mL of water, the temperature was decreased to 15° C., the pH was adjusted to 1.0-2.0; the solution was stirred for 12 h, the pH was adjusted to 3.0-4.0; stirred, filtered, dried at 30° C. under vacuum to give 0.61 g crystals, purity was 99.0% by HPLC, X-ray powder diffraction pattern showed crystal form I.

Example 5

The crude pyrroloquinoline quinone 1 g (HPLC purity >98%) was dissolved in a mixed solvent of water (100 mL) and ethanol (100 mL), the temperature was increased to 50° C., stirring was continued for 30 min, dissolved; filtered, the temperature was decreased to 15° C., the pH was adjusted to 1.0-2.0; the temperature was increased to 45° C. and the filtrate was crystallized under stirring at 45° C. for 12 h, the pH was adjusted to 3.0-4.0; stirred, filtered, dried at 25° C. under vacuum to give 0.80 g crystals, purity was 99.2% by HPLC, X-ray powder diffraction pattern showed crystal form I.

Example 6

The crude pyrroloquinoline quinone 1 g (HPLC purity >98%) was dissolved in a mixed solvent of water (100 mL) and ethanol (300 mL), the temperature was increased to 30° C., the pH was adjusted to 1.0-2.0; stirred for 12, the pH was adjusted to 3.0-4.0; stirred, filtered, dried at 45° C. under vacuum to give 0.85 g crystals, purity was 99.1% by HPLC, X-ray powder diffraction pattern showed crystal form I.

Example 7

The crude pyrroloquinoline quinone 1 g (HPLC purity >98%) was dissolved in a mixed solvent of water (100 mL) and ethanol (10 mL), the temperature was decreased to 15° C., the pH was adjusted to 1.0-2.0; stirred for 12, the pH was adjusted to 3.0-4.0; stirred, filtered, dried at 35° C. under vacuum to give 0.75 g crystals, purity was 98.7% by HPLC, X-ray powder diffraction pattern showed crystal form I.

Example 8

The crude pyrroloquinoline quinone 1 Kg (HPLC purity >98%) was dissolved in a mixed solvent of water (100 L) and ethanol (100 L), the temperature was increased to 50° C., stirring was continued for 30 min, dissolved; filtered, the temperature was decreased to 15° C., the pH was adjusted to 1.0-2.0; the temperature was increased to 45° C. and the filtrate was crystallized under stirring at 45° C. for 12 h, the pH was adjusted to 3.0-4.0; stirred, filtered, dried at 25° C. under vacuum to give 800 g crystals, purity was 99.1% by HPLC, X-ray powder diffraction pattern showed crystal form I.

The X-ray powder diffraction patterns of the products obtained in Examples 2 to 8 are the same as that in Example 1 and will not be repeatedly shown here.

Example 9

Figure 5:
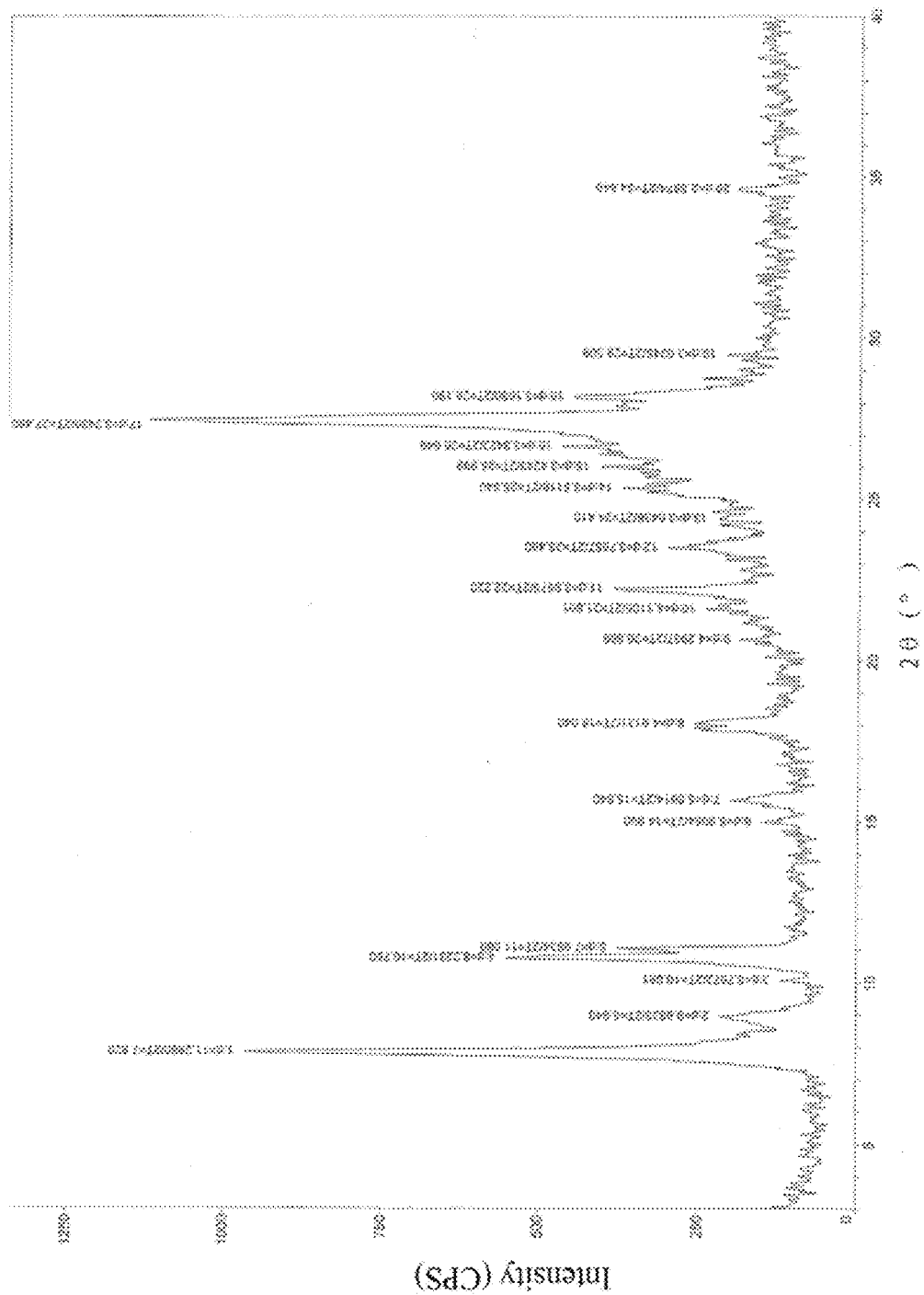
FIG. 5 is an X-ray powder diffraction pattern of crystal form II of pyrroloquinoline quinone disodium salt obtained in Example 9.
Figure 6:
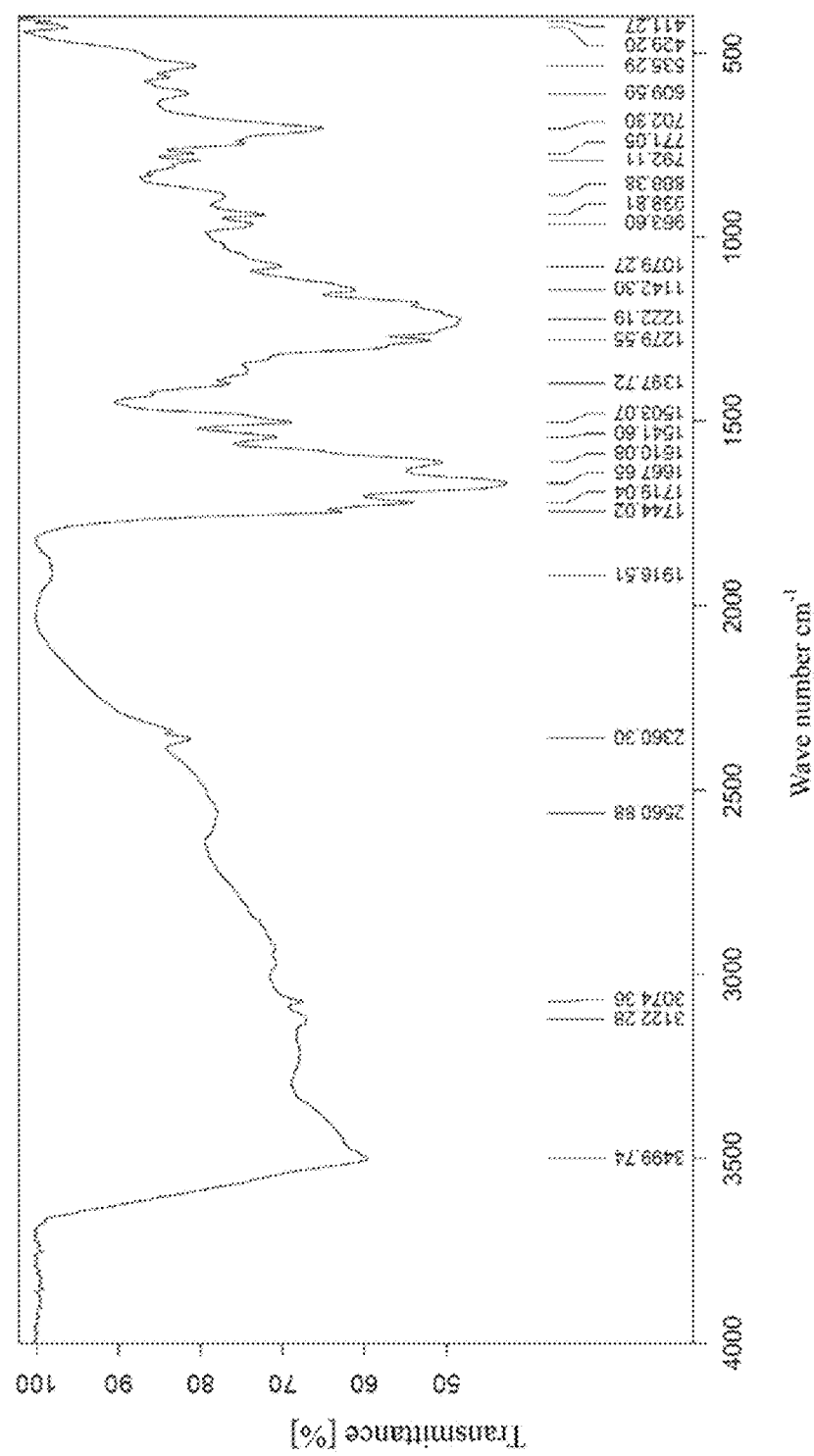
FIG. 6 is an infrared absorption spectrum of crystal form II of pyrroloquinoline quinone disodium salt obtained in Example 9.
Figure 7:
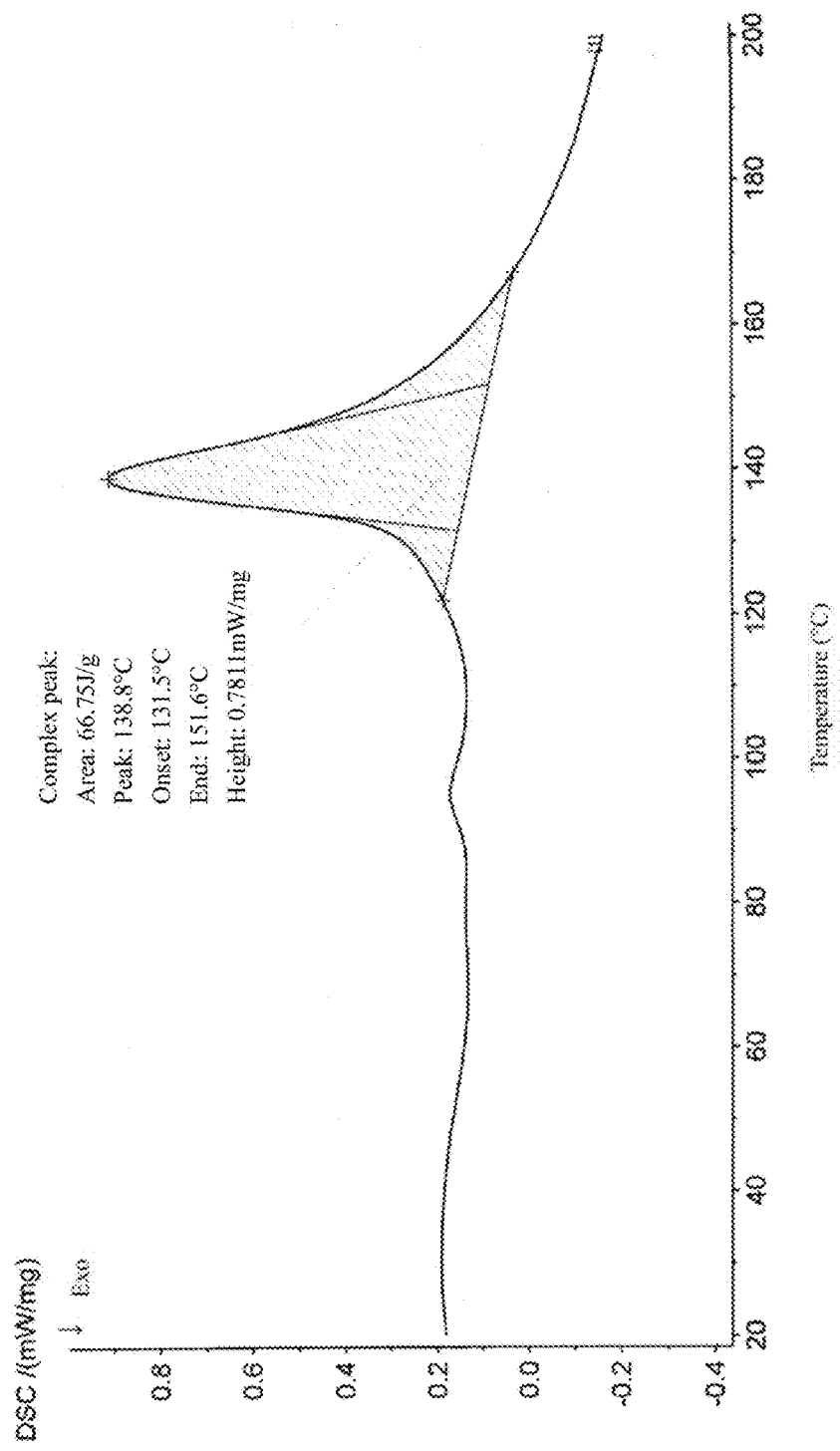
FIG. 7 is a DSC thermogram of crystal form II of pyrroloquinoline quinone disodium salt obtained in Example 9.
Figure 8:
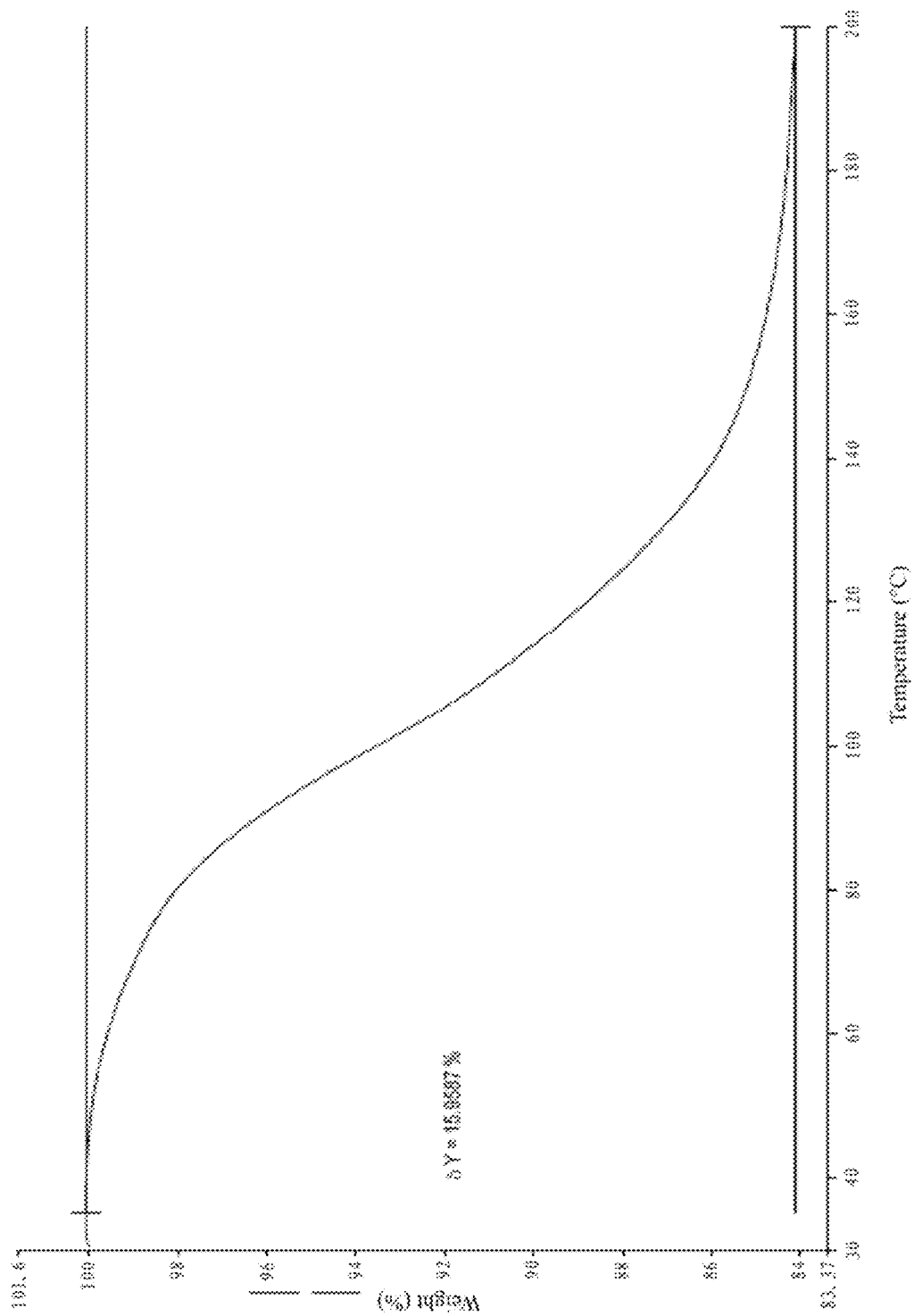
FIG. 8 is a TGA thermogram of crystal form II of pyrroloquinoline quinone disodium salt obtained in Example 9.
Figure 9:
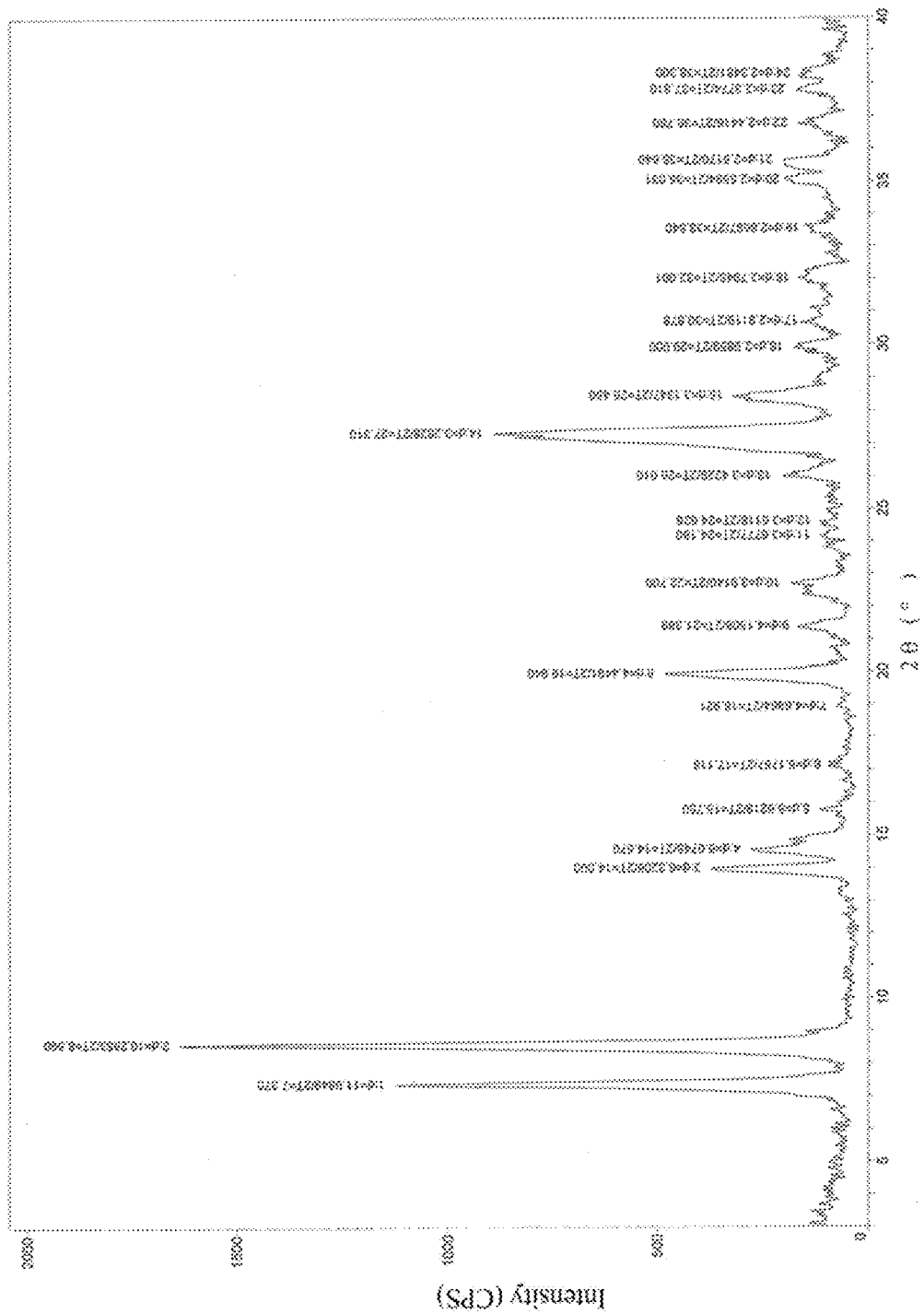
FIG. 9 is an X-ray powder diffraction pattern of crystal form III of pyrroloquinoline quinone disodium salt obtained in Example 11.

The crystal form I of pyrroloquinoline quinone disodium salt of Example 1 was dried at 60° C. for 8 hours to obtain a new crystal form. The X-ray powder diffraction pattern, the infrared absorption spectrum, DSC thermogram and TGA thermogram of the crystal form are detailed in FIGS. 5-9, the crystal form is named as crystal form II of pyrroloquinoline quinone disodium salt in the present invention.

Example 10

The crystal form I of pyrroloquinoline quinone disodium salt of Example 2 was dried at 30° C. for 8 hours to obtain the crystal form II of pyrroloquinoline quinone disodium salt.

The X-ray powder diffraction pattern of the product obtained in Example 10 is the same as that in Example 9 and will not be repeatedly shown here.

Example 11

Figure 10:
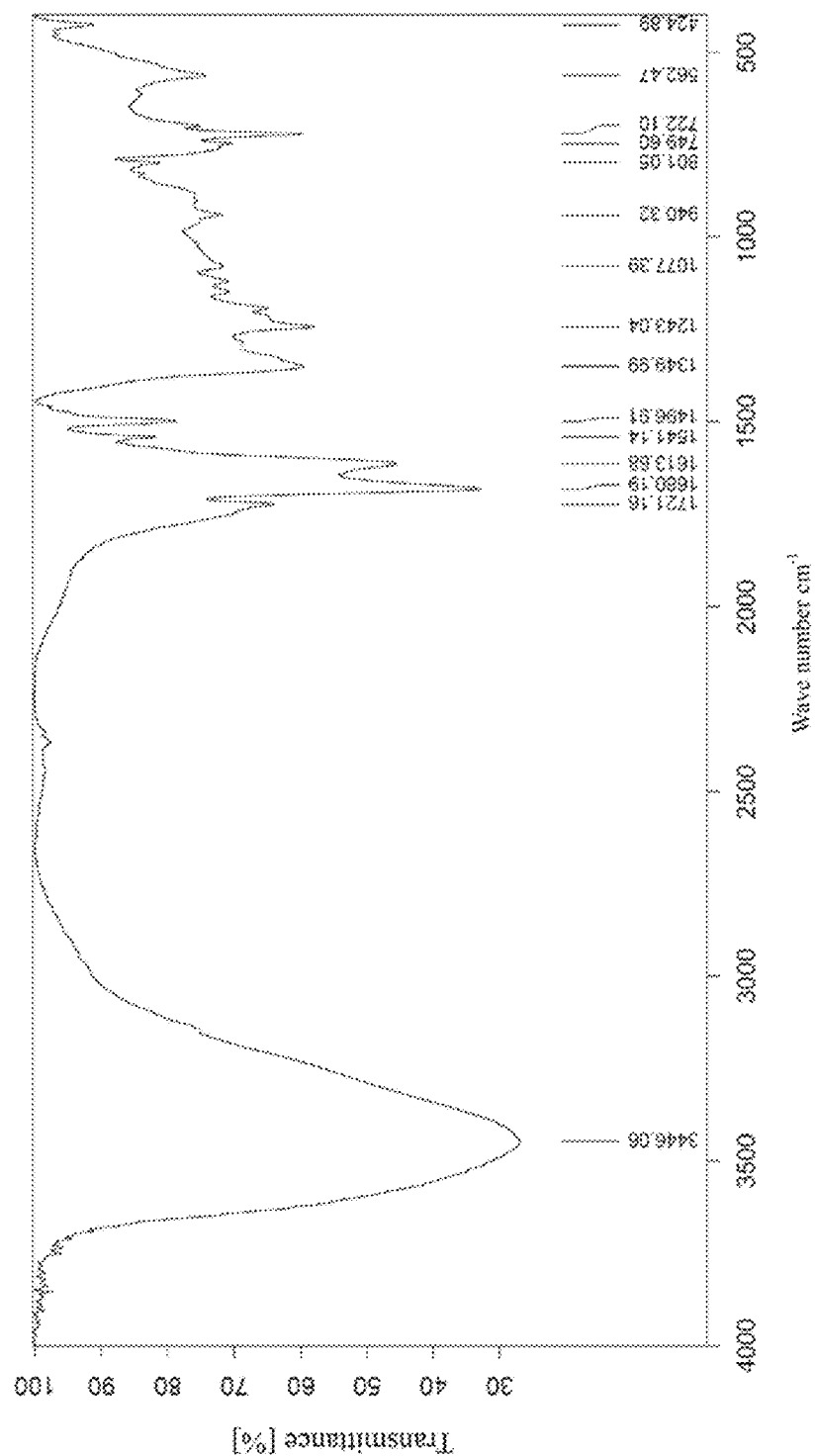
FIG. 10 is an infrared absorption spectrum of crystal form III of pyrroloquinoline quinone disodium salt obtained in Example 11.
Figure 11:
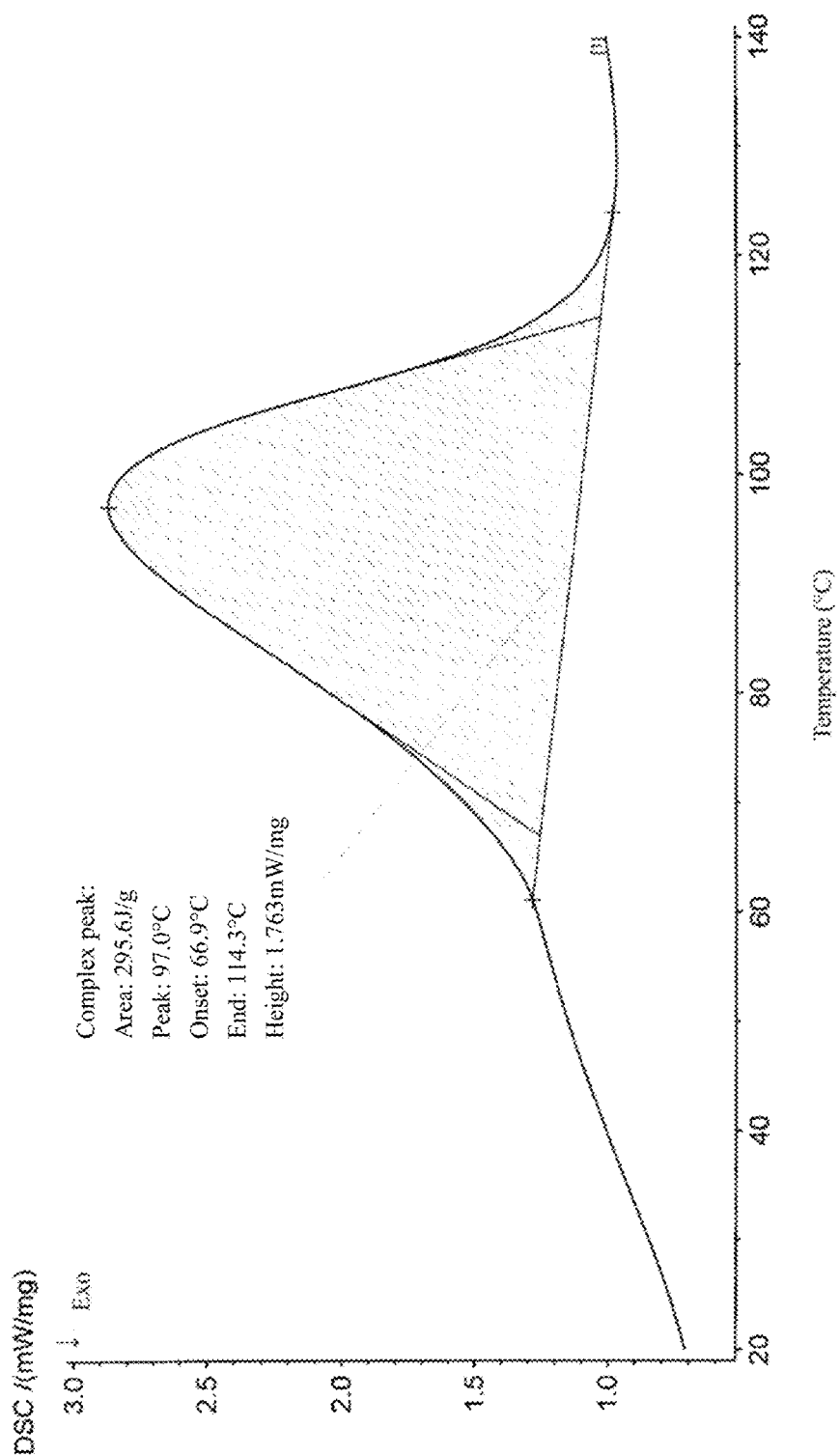
FIG. 11 is a DSC thermogram of crystal form III of pyrroloquinoline quinone disodium salt obtained in Example 11.
Figure 12:
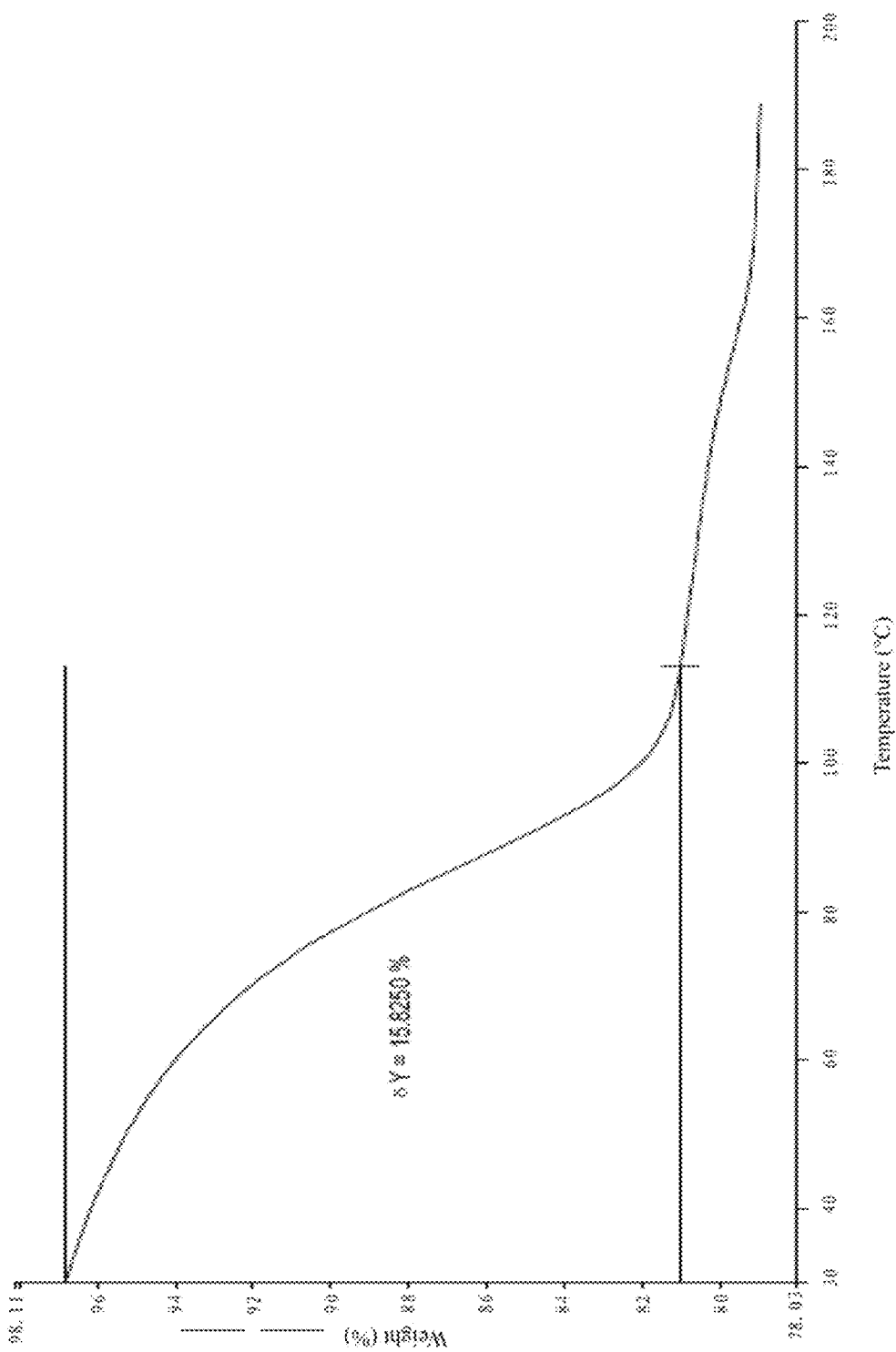
FIG. 12 is a TGA thermogram of crystal form III of pyrroloquinoline quinone disodium salt obtained in Example 11.

The crude pyrroloquinoline quinone 100 g (HPLC purity >98%) was dissolved in a mixed solvent of water (10 L) and ethanol (10 L), the temperature was increased to 50° C., stirring was continued for 30 min, dissolved; filtered, the temperature was decreased to 10° C., the pH was adjusted to 3.0-4.0; stirred, filtered, dried at 25° C. under vacuum to give 900 g crystals, purity was 98.7% by HPLC, X-ray powder diffraction pattern showed a new crystal form. The X-ray powder diffraction pattern, the infrared absorption spectrum, DSC thermogram and TGA thermogram of the crystal form are detailed in FIGS. 9-12, the crystal form is named as crystal form III of pyrroloquinoline quinone disodium salt in the present invention.

Example 12

The crude pyrroloquinoline quinone 100 g (HPLC purity >98%) was dissolved in a mixed solvent of water (10 L) and ethanol (30 L), the temperature was increased to 50° C., stirring was continued for 30 min, dissolved; filtered, the temperature was decreased to 20° C., the pH was adjusted to 3.0-4.0; stirred, filtered, dried at 25° C. under vacuum to give 920 g crystals, purity was 98.7% by HPLC, X-ray powder diffraction pattern showed crystal form III.

Example 13

The crude pyrroloquinoline quinone 100 g (HPLC purity >98%) was dissolved in a mixed solvent of water (10 L) and ethanol (20 L), the temperature was increased to 50° C., stirring was continued for 30 min, dissolved; filtered, the temperature was decreased to 0° C., the pH was adjusted to 3.0-4.0; stirred, filtered, dried at 25° C. under vacuum to give 930 g crystals, purity was 98.7% by HPLC, X-ray powder diffraction pattern showed crystal form III.

Example 14

The pyrroloquinoline quinone trisodium salt solution 100 g (HPLC purity >98%, concentration 0.7%) was heated up to 40° C., stirring was continued for 30 min, the pH was adjusted to 1.0-2.0; filtered to give a clear filtrate, the temperature of the filtrate was decreased to 25° C. with the rate of 10° C./h, and the filtrate was crystallized under stirring at 25° C. for 12 h, filtered, dried at 25° C. under vacuum to give 0.9 g crystals, purity was 99.4% by HPLC, X-ray powder diffraction pattern showed a new crystal form.

Figure 13:
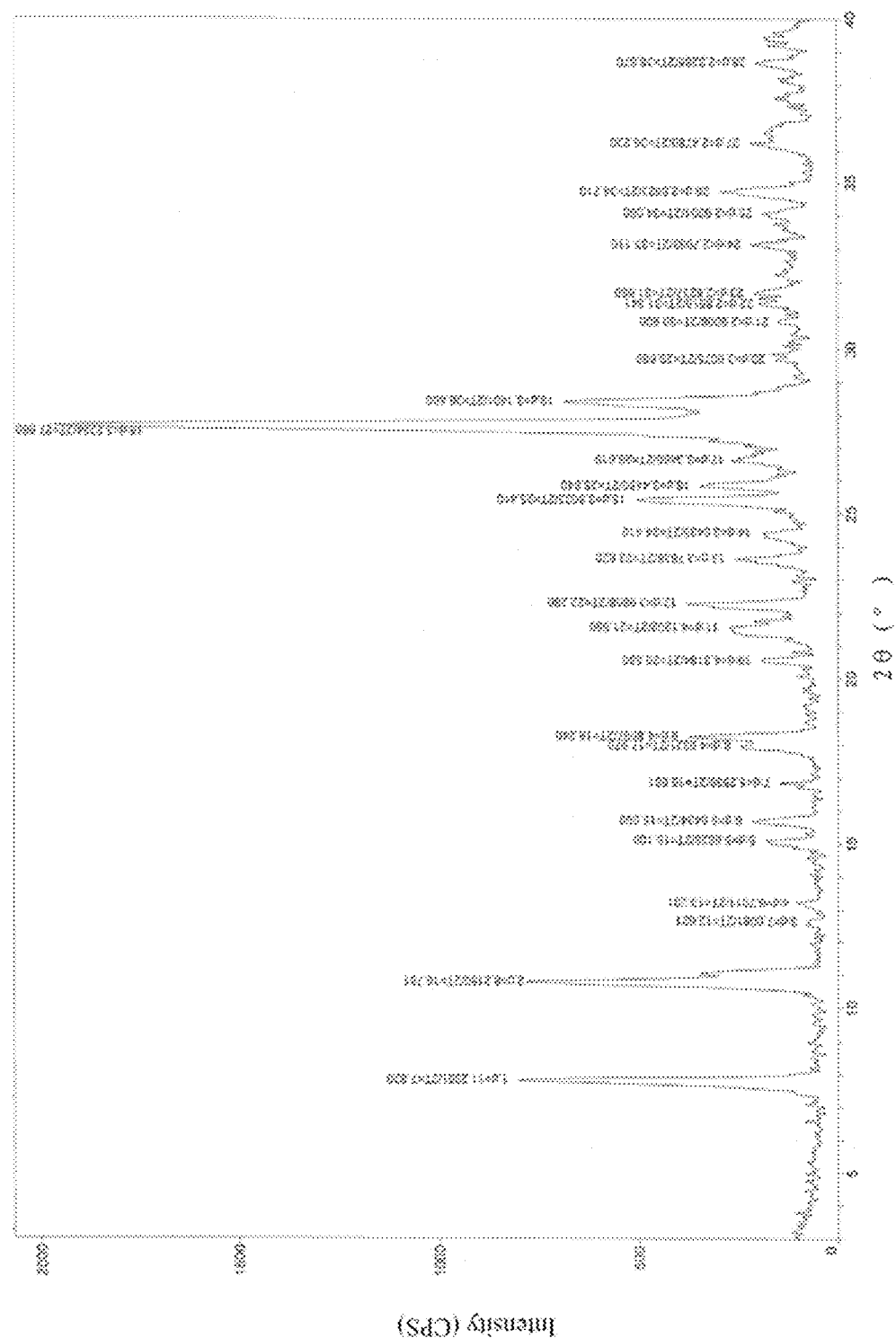
FIG. 13 is an X-ray powder diffraction pattern of crystal form IV of pyrroloquinoline quinone monosodium salt obtained in Example 14.
Figure 14:
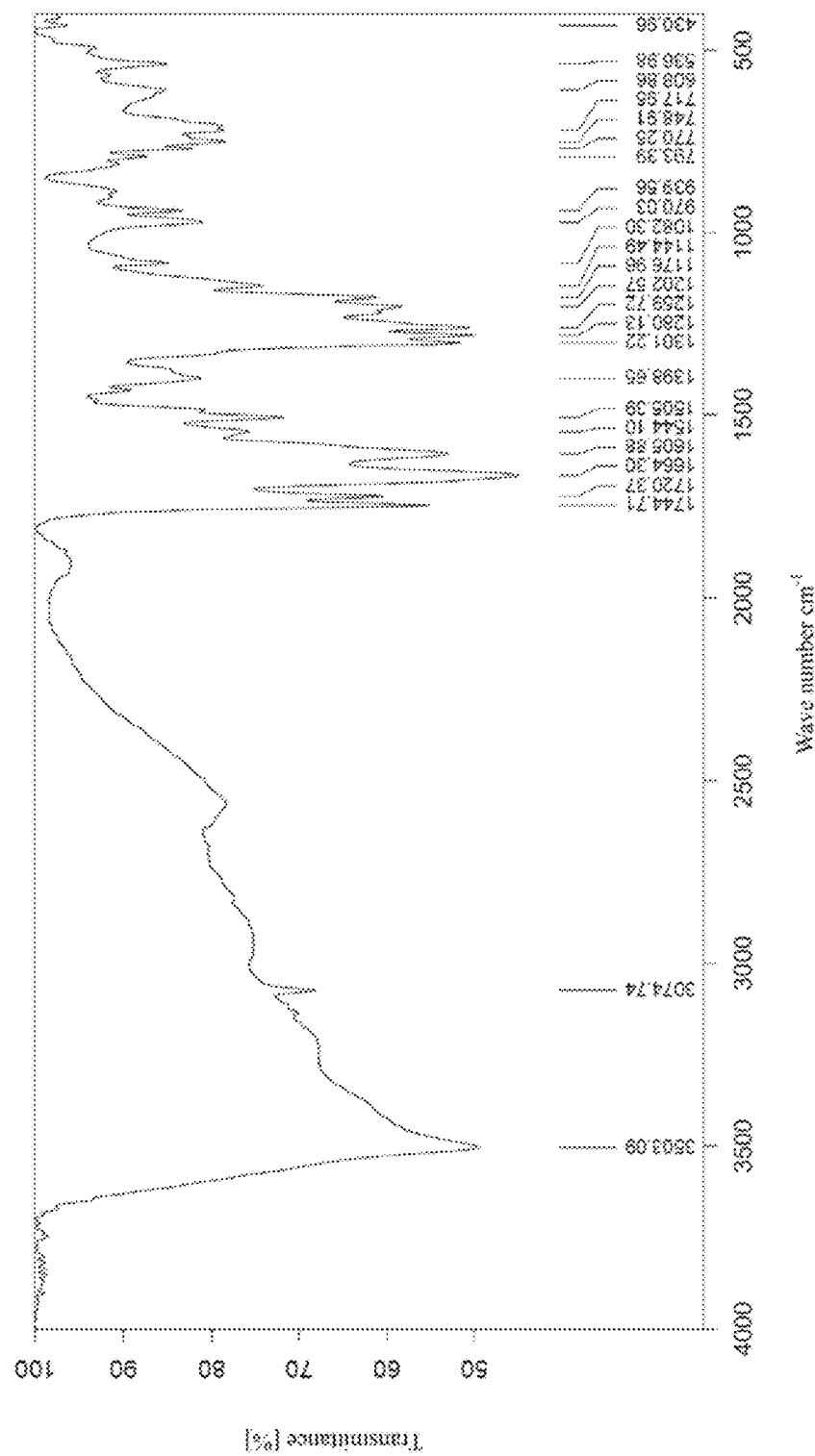
FIG. 14 is an infrared absorption spectrum of crystal form IV of pyrroloquinoline quinone monosodium salt obtained in Example 14.
Figure 15:
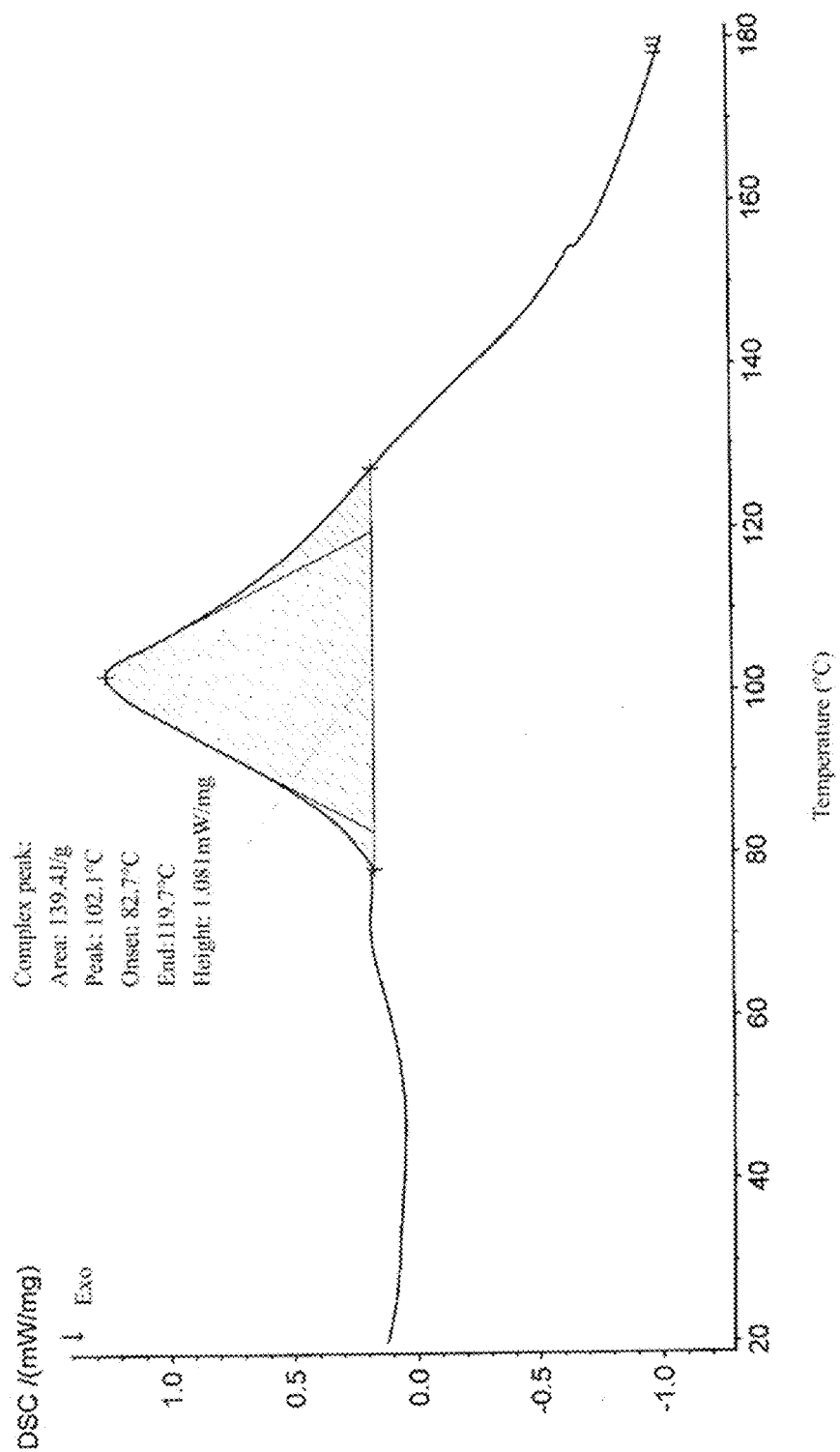
FIG. 15 is a DSC thermogram of crystal form IV of pyrroloquinoline quinone monosodium salt obtained in Example 14.
Figure 16:
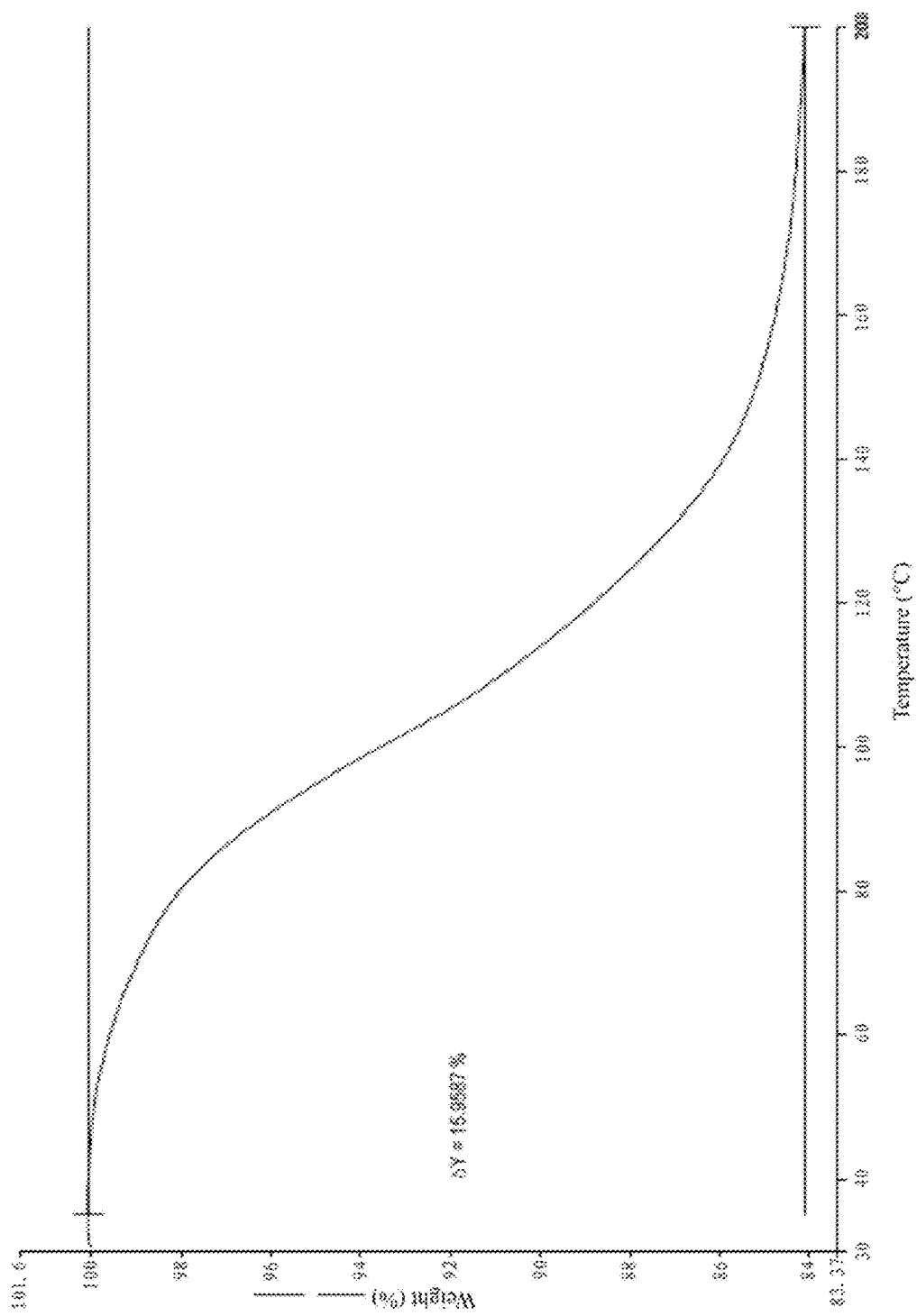
FIG. 16 is a TGA thermogram of crystal form IV of pyrroloquinoline quinone monosodium salt obtained in Example 14.

The X-ray powder diffraction pattern, the infrared absorption spectrum, DSC thermogram and TGA thermogram of the crystal form are detailed in FIGS. 13-16, the crystal form is named as crystal form IV of pyrroloquinoline quinone monosodium salt in the present invention.

Example 15

The crude pyrroloquinoline quinone 1 g (HPLC purity >98%) was dissolved in 100 mL of water, the temperature was increased to 60° C., stirring was continued for 30 min, dissolved; filtered, the pH was adjusted to 1.0-2.0; filtered to give a clear filtrate, the temperature of the filtrate was decreased to 25° C. with the rate of 10° C./h, and the filtrate was crystallized under stirring at 25° C. for 48 h, filtered, dried at 25° C. under vacuum to give 0.72 g crystals, purity was 99.1% by HPLC, X-ray powder diffraction pattern showed crystal form IV.

Example 16

The crude pyrroloquinoline quinone 1 g (HPLC purity >98%) was dissolved in 100 mL of water, the temperature was increased to 40° C., stirring was continued for 30 min, dissolved; filtered, the temperature was decreased to 15° C., the pH was adjusted to 1.0-2.0; stirred for 12 h, filtered, dried at 25° C. under vacuum to give 0.71 g crystals, purity was 99.2% by HPLC, X-ray powder diffraction pattern showed crystal form IV.

Example 17

The crude pyrroloquinoline quinone 1 g (HPLC purity >98%) was dissolved in 100 mL of water, the temperature was decreased to 15° C., the pH was adjusted to 1.0-2.0; stirred for 12 h, filtered, dried at 30° C. under vacuum to give 0.88 g crystals, purity was 99.0% by HPLC, X-ray powder diffraction pattern showed crystal form IV.

The X-ray powder diffraction patterns of the products obtained in Examples 15 to 17 are the same as that in Example 14 and will not be repeatedly shown here.

Example 18

Hygroscopicity test. Test Conditions: watch glasses were placed in the environment at the temperature of 25° C. and the humidity of 75% for 24 h, then for each of the following samples, 1 g was weighed, and the weighted samples were quickly placed in the environment at the temperature of 25° C. and the humidity of 75% for 24 h to absorb moisture sufficiently. The results are as follows:

| Crystal form | Weight before absorbing moisture | Weight after absorbing moisture | Rate of moisture absorption |
|---|---|---|---|
| Crystal form I | 1.0050 g | 1.0050 g | 0% |
| Crystal form II | 1.0062 g | 1.0092 g | 0.30% |
| Crystal form III | 1.0034 g | 1.0034 g | 0% |
| Crystal form IV | 1.0025 g | 1.0025 g | 0% |
| Crystal form of the disodium salt in CN201080031945 | 1.0031 g | 1.0117 g | 0.85% |

From the above experimental data, it can be seen that the crystal form I, the crystal form III and the crystal form IV are not hygroscopic and have good stabilities, followed by the crystal form II, and the crystal form in CN201080031945 has the strongest hygroscopicity. Therefore, the new crystal forms developed by the present invention are not easy to exchange material with the environment and can maintain good stabilities.

In addition, from the pictures of crystal habits in FIG. 17, it can be seen that the crystal form I, the crystal form II and the crystal form IV of the present invention are rhombohedral, the crystal form III is needle-like, the crystal form I, the crystal form II, the crystal form III and the crystal form IV have regular crystal habits, they are easy to be filtered and washed, can effectively reduce the amount of residual solution in the solid, effectively improve the purity of the products, reduce solvent residues, they are conducive to drying and have small specific surface area per unit volume and low surface energy, and the contact surfaces of the crystals with the environment are small, which are conducive to material stabilities. In addition, the crystal form I and the crystal form II of the present invention can be prepared without using organic solvents, thereby effectively avoiding the solvent residues in the samples, reducing the production cost and reducing the solvent recovery cost, and the process is more environment-friendly.

In summary, through an extensive study, the inventors of the present invention found the new crystal forms of pyrroloquinoline quinone disodium salt of the present invention, they have good solubilities, simple crystallization process, easy operation, low pollution, and industrialized production can be achieved. In addition, the drugs in the crystal forms of the present invention have the advantages of high product purities, excellent physical and chemical properties, good chemical stabilities and can be reproduced through processing (filtering, drying, dissolving and tabletting).

The invention claimed is:

1. A crystal form III of pyrroloquinoline quinone disodium salt, wherein Cu target is used, and the X-ray powder diffraction pattern of the crystal form III has characteristic peaks at the following 2θ diffraction angles: 7.4±0.2°, 8.6±0.2°, 14.0±0.2°, 14.6±0.2°, 19.9±0.2°, 21.4±0.2°, 26.0±0.2°, 27.3±0.2° and 28.5±0.2°.

2. A method for preparing the crystal form III of pyrroloquinoline quinone disodium salt according to claim 1, wherein said method comprises the following steps:
  (1) adding pyrroloquinoline quinone trisodium salt to a mixed solvent of ethanol/water;
  (2) stirring, dissolving with the temperature increased to about 50° C.;
  (3) reducing the temperature to 0° C.-20° C., then adjusting the pH to 3-4;
  (4) crystallizing; and
  (5) filtering to give the crystal form III of pyrroloquinoline quinone disodium salt.

3. The method according to claim 2, wherein with g/ml as the unit, the weight-to-volume ratio of pyrroloquinoline quinone to the mixed solvent of ethanol/water is from 1:200 to 1:400, wherein the volume ratio of ethanol to water is 1:1-3:1, and the temperature of crystallization is controlled at 0° C.-20° C.

4. A pharmaceutical composition, a cosmetic composition, or a functional food or nutritional agent comprising the crystal form III of pyrroloquinoline quinone disodium salt according to claim 1.

5. The crystal form III of pyrroloquinoline quinone disodium salt according to claim 1, for use in a medicine, a functional food or a cosmetic.

6. The method according to claim 3, wherein the temperature of crystallization is controlled at 5° C.-15° C.

* * * * *